United States Patent [19]
Heim et al.

[11] Patent Number: 5,922,569
[45] Date of Patent: *Jul. 13, 1999

[54] PROCESS FOR THE PRODUCTION OF POLYPEPTIDES

[75] Inventors: Jutta Heim, Ramlinsburg; Thomas Hottiger, Sissach; Gabriele Pohlig, Riehen; Peter Fürst, Basle, all of Switzerland

[73] Assignee: Ciba-Geigy Corporation, Tarrytown, N.Y.

[ * ] Notice: This patent is subject to a terminal disclaimer.

[21] Appl. No.: 08/453,051

[22] Filed: May 26, 1995

Related U.S. Application Data

[63] Continuation of application No. 08/165,720, Dec. 10, 1993, abandoned.

[30] Foreign Application Priority Data

Dec. 15, 1992 [GB] United Kingdom ................. 92811005

[51] Int. Cl.⁶ .............................. C12P 21/02; C12N 1/19; C12N 15/81
[52] U.S. Cl. .................................... 435/69.2; 435/254.21; 435/320.1
[58] Field of Search ................................. 435/69.1, 69.9, 435/254, 256, 320.1, 69.2, 254.21; 536/24.1

[56] References Cited

U.S. PATENT DOCUMENTS

| | | | |
|---|---|---|---|
| 4,870,008 | 9/1989 | Brake et al. | 435/69.4 |
| 4,935,350 | 6/1990 | Patel et al. | |
| 4,940,661 | 7/1990 | Etcheverry et al. | |
| 5,162,208 | 11/1992 | Lemoine et al. | 435/69.1 |

FOREIGN PATENT DOCUMENTS

| | | |
|---|---|---|
| 0 134 773 | 3/1985 | European Pat. Off. |
| 0 252 854 | 1/1988 | European Pat. Off. |
| 0 310 586 | 4/1989 | European Pat. Off. |
| 0 340 170 | 11/1989 | European Pat. Off. |
| 0 341 215 | 11/1989 | European Pat. Off. |

OTHER PUBLICATIONS

Derwent Abstract #AU–D–1584588, "Gene Expression System Contains Yeast Copper Resistance Gene and Multiple Cloning Site and is Movable as Cassette", Nov. 10, 1988.
Huibregtse et al., *PNAS*, "Copper–induced Binding of Cellular Factors to Yeast Metallothionein Upstream Activation Sequences", 86:65–69 (1989).
Welch et al., *EMBO*, "The CUP2 Gene Product Regulates the Expression of the CUP1 Gene, Coding for Yeast Metallothionein", 8(1) 255–260 (1989).
Beyreuther, K. (1980) in "The Operon" et. Miller et al CSH Press, Cold Spring Harbor, N.Y., p. 123–124.
Bruschi et al. (1989), Current Genet. 15, 83–90.
Etcheverry (1990). in "Methods in Enzymol.", vol. 185 p. 319–329, Academ. PR., N.Y.
Eugster et. al. (1990). Biochem. Biophys. Res. Comm. 172(2), 737–744.
Macreadie et. al. (1991). Gene 104, 107–111.
Moir et al. (1991) in "Methods in Enzymol." vol. 194, p. 491–507, Academ. PR., N.Y.
Takabayashi et al. (1990). Yeast 6, S490(Abstract.)
Butt, T.R. et al., "Copper metallothionein of yeast, structure of the gene, and regulation of expression", *Proc. Nat'l Acad. Sc: USA*, 81: 3332–3336 (1984).
Butt, T.R. et al., "Cloning and expression of a yeast copper metallothionein gene", *Gene*, 27: 23–33 (1984).
Butt, T.R. et al., "Yeast Metallothionein and Applications in Biotechnology", *Microbiological Reviews*, 51: 351–364 (1987.
Fürst, P. et al., "Copper activates Metallothionein Gene Transcription by Altering the Conformation of a Specific DNA Binding Protein", *Cell*, 55: 705–717 (1988).
Hamer, D.H. et al, "Function and Autoregulation of Yeast Copperthionein", *Science* 228: 685–690 (1985).
Hanahan, D., "Studies on Transformation of *Escherichia coli* with Plasmids", *J. Mol. Biol.* 166:557–580 (1983).
Henderson, R.C.A. et al., "The transformation of brewing yeasts with a plasmid containing the gene for copper resistance", *Current Genetics* 9: 133–138 (1985).
Hinnen, A. et al., "Transformation of Yeast", *Proc. Natl. Acad. Sci. USA* 75 (4): 1929–1933 (1978).
Mead, D.A. et al., "Single–stranded DNA 'blue' T7 promoter plasmids: a versatile tandem promoter system for cloning and protein engineering", *Protein Engineering* 1 (1): 67–74 (1986).
Rudolph, H. et al., "One–step gene replacement in yeast by cotransformation", *Gene* 36: 87–95 (1985).
Scharf, M. et al., "Primary structures of new 'iso–hirudins'", *FEBS Letters* 255 (1): 105–110 (1989).
Sherman, F., "Getting Started with Yeast", *Method in Enzymology* 194: 3–21 (1991).
Thiele, D.J. et al., "Mammalian Metallothionein is Functional in Yeast", *Science* 231: 854–856 (1986).
Wright, C.F. et al. "Chromogenic identification of oligonucleotide–directd mutants", *Nucleic Acids Research* 14 (21): 8489–8499 (1986).
Zoller, M.J. et al. "Oligonucleotide–Directed Mutagenesis of DNA Fragments Cloned into M13 Vectors", *Methods in Enzymology* 100: 468–500 (1983).

*Primary Examiner*—James Ketter
*Attorney, Agent, or Firm*—Henry P. Nowak; James Scott Elmer; W. Murray Spruill

[57] ABSTRACT

The invention concerns a method for the production of a polypeptide with the aid of genetically engineered yeast cells which contain not more than one functional CUP1 gene in the genome and carry a plasmid comprising a gene coding for said polypeptide and a functional CUP1 gene; and said yeast cells and said plasmids.

20 Claims, 7 Drawing Sheets

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 1318 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: misc_feature
      (B) LOCATION: 1..6
      (D) OTHER INFORMATION: /function= "BamHI linker"

(ix) FEATURE:
     (A) NAME/KEY: promoter
     (B) LOCATION: 7..460
     (D) OTHER INFORMATION: /standard_name= "CUP1 promoter"

(ix) FEATURE:
     (A) NAME/KEY: CDS
     (B) LOCATION: 461..646
     (D) OTHER INFORMATION: /product= "methallothionein"

(ix) FEATURE:
     (A) NAME/KEY: terminator
     (B) LOCATION: 647..1312
     (D) OTHER INFORMATION: /standard_name= "CUP1 transcription
         termination sequence"

(ix) FEATURE:
     (A) NAME/KEY: misc_feature
     (B) LOCATION: 1313..1318
     (D) OTHER INFORMATION: /function= "BamHI linker"

(xi) SEQUENCE DESCRIPTION: SEQ ID NO:1:

```
GGATCCCCAT TACCGACATT TGGGCGCTAT ACGTGCATAT GTTCATGTAT GTATCTGTAT    60

TTAAAACACT TTTGTATTAT TTTTCCTCAT ATATGTGTAT AGGTTTATAC GGATGATTTA   120

ATTATTACTT CACCACCCTT TATTTCAGGC TGATATCTTA GCCTTGTTAC TAGTTAGAAA   180

AAGACATTTT TGCTGTCAGT CACTGTCAAG AGATTCTTTT GCTGGCATTT CTTCTAGAAG   240

CAAAAGAGC GATGCGTCTT TTCCGCGGAA CCGTTCCAGC AAAAAAGACT ACCAACGCAA    300

TATGGATTGT CAGAATCATA TAAAAGAGAA GCAAATAACT CCTTGTCTTG TATCAATTGC   360

ATTATAATAT CTTCTTGTTA GTGCAATATC ATATAGAAGT CATCGAAATA GATATTAAGA   420

AAAACAAACT GTACAATCAA TCAATCAATC ATCACATAAA ATG TTC AGC GAA TTA    475
                                              Met Phe Ser Glu Leu
                                               1                 5

ATT AAC TTC CAA AAT GAA GGT CAT GAG TGC CAA TGC CAA TGT GGT AGC    523
Ile Asn Phe Gln Asn Glu Gly His Glu Cys Gln Cys Gln Cys Gly Ser
              10                  15                  20

TGC AAA AAT AAT GAA CAA TGC CAA AAA TCA TGT AGC TGC CCA ACG GGG    571
Cys Lys Asn Asn Glu Gln Cys Gln Lys Ser Cys Ser Cys Pro Thr Gly
         25                  30                  35

TGT AAC AGC GAC GAC AAA TGC CCC TGC GGT AAC AAG TCT GAA GAA ACC    619
Cys Asn Ser Asp Asp Lys Cys Pro Cys Gly Asn Lys Ser Glu Glu Thr
     40                  45                  50

AAG AAG TCA TGC TGC TCT GGG AAA TGAAACCGCG GGTCTTTAAT ATATTCATCT    673
Lys Lys Ser Cys Cys Ser Gly Lys
 55                  60

AACTATTTGC TGTTTTTAAT TTTTAAAAGG AGAAGGAAGT TTAATCGACG ATTCTACTCA   733

GTTTGAGTAC ACTTATGTAT TTTGTTTAGA TACTTTGTTA ATTTATAGGT ATACGTTAAT   793

AATTAAGAAA AGGAAATAAA GTATCTCCAT ATGTCGCCCC AAGAATAAAA TATTATTACC   853

AAATTCTAGT TTGCCTAACT TACAACTCTG TATAGAATCC CCAGATTTCG AATAAAAAAA   913

AAAAAAAAAG CTATTCATGG TACCCGCTGC TGAAAACCTA TCTCCGATAC CTGCCTCTAT   973

TGATACGAAC GACATTCCTT TAATTGCTAA CGATTTAAAA TTACTGGAAA CGCAAGCAAA  1033

ATTGATAAAT ATTCTGCAAG GTGTTCCTTT CTACTTGCCA GTAAATTTAA CCAAAATTGA  1093

AAGTCTGATA GAAACCTTGA CTATGGGCGT GAGTAATACA GTAGACTTAT ATTTTCATGA  1153

CAACGAAGTC AGAAAAGAAT GGAAAGACAC TTTAAATTTT ATCAATACCA TTGTTTATAC  1213

AAATTTTTTC CTTTTTGTTC AAAACGAATC CTCTTTGTCC ATGGCAGTTC AACATTCTTC  1273

TAACAACAAT AAGACCTCGA ACTCTGAAAG ATGTGCAAAG GATCC                  1318
```

(2) INFORMATION FOR SEQ ID NO:2:

(i) SEQUENCE CHARACTERISTICS:
        (A) LENGTH: 61 amino acids
        (B) TYPE: amino acid
        (D) TOPOLOGY: linear (ii) MOLECULE TYPE: protein (xi) SEQUENCE DESCRIPTION: SEQ ID NO:2:

```
Met Phe Ser Glu Leu Ile Asn Phe Gln Asn Glu Gly His Glu Cys Gln
 1               5                  10                  15

Cys Gln Cys Gly Ser Cys Lys Asn Asn Glu Gln Cys Gln Lys Ser Cys
             20                  25                  30

Ser Cys Pro Thr Gly Cys Asn Ser Asp Asp Lys Cys Pro Cys Gly Asn
         35                  40                  45

Lys Ser Glu Glu Thr Lys Lys Ser Cys Cys Ser Gly Lys
     50                  55                  60
```

(2) INFORMATION FOR SEQ ID NO:3:

(i) SEQUENCE CHARACTERISTICS:
        (A) LENGTH: 1082 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..6
        (D) OTHER INFORMATION: /function= "BamHI linker"

(ix) FEATURE:
        (A) NAME/KEY: promoter
        (B) LOCATION: 7..432
        (D) OTHER INFORMATION: /standard_name= "CUP1 promoter"

(ix) FEATURE:
        (A) NAME/KEY: misc_feature
        (B) LOCATION: 433..441
        (D) OTHER INFORMATION: /function= "EcoRI linker"

(ix) FEATURE:
        (A) NAME/KEY: sig_peptide
        (B) LOCATION: 442..492
        (D) OTHER INFORMATION: /standard_name= "PHO5 signal
           sequence"

(ix) FEATURE:
        (A) NAME/KEY: mat_peptide
        (B) LOCATION: 493..690
        (D) OTHER INFORMATION: /product= "desulphatohirudin"
           /standard_name= "HV1"

(ix) FEATURE:
        (A) NAME/KEY: terminator
        (B) LOCATION: 691..1068
        (D) OTHER INFORMATION: /standard_name= "PHO5 terminator"

(ix) FEATURE:
        (A) NAME/KEY: misc_feature
        (B) LOCATION: 1069..1082
        (D) OTHER INFORMATION: /function= "SalI linker"

(ix) FEATURE:
        (A) NAME/KEY: CDS
        (B) LOCATION: 442..690
        (D) OTHER INFORMATION: /product= "primary transcript"

(xi) SEQUENCE DESCRIPTION: SEQ ID NO:3:

```
GGATCCCCAT TACCGACATT TGGGCGCTAT ACGTGCATAT GTTCATGTAT GTATCTGTAT      60

TTAAAACACT TTTGTATTAT TTTTCCTCAT ATATGTGTAT AGGTTTATAC GGATGATTTA     120

ATTATTACTT CACCACCCTT TATTTCAGGC TGATATCTTA GCCTTGTTAC TAGTTAGAAA     180

AAGACATTTT TGCTGTCAGT CACTGTCAAG AGATTCTTTT GCTGGCATTT CTTCTAGAAG     240

CAAAAGAGC GATGCGTCTT TTCCGCTGAA CCGTTCCAGC AAAAAAGACT ACCAACGCAA      300

TATGGATTGT CAGAATCATA TAAAAGAGAA GCAAATAACT CCTTGTCTTG TATCAATTGC     360

ATTATAATAT CTTCTTGTTA GTGCAATATC ATATAGAAGT CATCGAAATA GATATTAAGA    420

AAAACAAACT GTGAATTCAA A ATG TTT AAA TCT GTT GTT TAT TCA ATT TTA       471
                        Met Phe Lys Ser Val Val Tyr Ser Ile Leu
                        -17     -15             -10
```

```
GCC GCT TCT TTG GCC AAT GCA GTT GTT TAC ACC GAC TGT ACC GAA TCT       519
Ala Ala Ser Leu Ala Asn Ala Val Val Tyr Thr Asp Cys Thr Glu Ser
             -5               1                 5
```

```
GGT CAA AAC TTG TGT TTG TGT GAA GGT TCT AAC GTT TGT GGT CAA GGT       567
Gly Gln Asn Leu Cys Leu Cys Glu Gly Ser Asn Val Cys Gly Gln Gly
 10             15                  20                  25
```

```
AAC AAG TGT ATC TTG GGT TCT GAC GGT GAA AAG AAC CAA TGT GTT ACC       615
Asn Lys Cys Ile Leu Gly Ser Asp Gly Glu Lys Asn Gln Cys Val Thr
             30                  35                  40
```

```
GGT GAA GGT ACC CCA AAG CCA CAA TCT CAC AAC GAC GGT GAC TTC GAA       663
Gly Glu Gly Thr Pro Lys Pro Gln Ser His Asn Asp Gly Asp Phe Glu
             45                  50                  55
```

```
GAA ATC CCA GAA GAA TAC TTG CAA TAGGATCCTG GTACGTTCCT CAAGGTGCTC      717
Glu Ile Pro Glu Glu Tyr Leu Gln
             60             65
```

```
GTGTCTACAC CGAAAAATTC CAATGTTCTA ACGACACCTA CGTCAGATAC GTCATTAACG     777

ATGCTGTTGT TCCAATTGAA ACCTGTTCCA CTGGTCCAGG GTTCTCTTGT GAAATCAATG     837

ACTTCTACGA CTATGCTGAA AAGAGAGTAG CCGGTACTGA CTTCCTAAAG GTCTGTAACG     897

TCAGCAGCGT CAGTAACTCT ACTGAATTGA CCTTCTACTG GGACTGGAAC ACTACTCATT     957

ACAACGCCAG TCTATTGAGA CAATAGTTTT GTATAACTAA ATAATATTGG AAACTAAATA    1017

CGAATACCCA AATTTTTTAT CTAAATTTTG CCGAAAGATT AAAATCTGCA GCCAAGCTGG    1077

TCGAC                                                                1082
```

(2) INFORMATION FOR SEQ ID NO:4:

(i) SEQUENCE CHARACTERISTICS:
        (A) LENGTH: 82 amino acids
        (B) TYPE: amino acid
        (D) TOPOLOGY: linear (ii) MOLECULE TYPE: protein (xi) SEQUENCE DESCRIPTION: SEQ ID NO:4:

```
Met Phe Lys Ser Val Val Tyr Ser Ile Leu Ala Ala Ser Leu Ala Asn
-17     -15             -10                 -5

Ala Val Val Tyr Thr Asp Cys Thr Glu Ser Gly Gln Asn Leu Cys Leu
     1               5                  10                  15

Cys Glu Gly Ser Asn Val Cys Gly Gln Gly Asn Lys Cys Ile Leu Gly
             20                  25                  30

Ser Asp Gly Glu Lys Asn Gln Cys Val Thr Gly Glu Gly Thr Pro Lys
             35                  40                  45
```

-continued

```
Pro Gln Ser His Asn Asp Gly Asp Phe Glu Glu Ile Pro Glu Glu Tyr
        50                  55                  60

Leu Gln
    65

(2) INFORMATION FOR SEQ ID NO:5:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..28
        (D) OTHER INFORMATION: /function= "primer for PCR"

(xi) SEQUENCE DESCRIPTION: SEQ ID NO:5:

GGATCCATTA CCGACATTTG GGCGCTAT                                              28

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..30
        (D) OTHER INFORMATION: /function= "primer for PCR"

(xi) SEQUENCE DESCRIPTION: SEQ ID NO:6:

GAATTCACAG TTTGTTTTTC TTAATATCTA                                            30
```

PROCESS FOR THE PRODUCTION OF POLYPEPTIDES

This application is a continuation of application Ser. No. 08/165,720, filed Dec. 10, 1993, abandoned.

The invention pertains to the field of recombinant DNA technology and concerns a method for the production of polypeptides with the aid of genetically engineered yeast cells carrying hybrid vectors comprising the genes for said polypeptides, said hybrid vectors and yeast cells, and methods for the preparation of said vectors and yeast cells.

BACKGROUND OF THE INVENTION

Although in genetic engineering numerous polypeptide expression systems for prokaryotic and eukaryotic hosts are already known, there is a continuing demand for novel systems which have advantages over the known systems.

Very widely used as hosts for the production of polypeptides are yeasts, e.g. *Saccharomyces cerevisiae,* for which different types of vectors exist.

Integrating vectors which do not contain an autonomously replicating sequence (ARS). These vectors have usually low transformation rates and usually lead to single copy integration into the yeast genome.

Extrachromosomally replicating vectors which can be subdivided in:

Vectors containing autonomously replicating sequences (ars vectors). These vectors are usually present in high copy numbers in the cell, however, they are frequently lost during cell division.

Vectors containing a DNA sequence acting as a centromer during cell division (cen vectors). These vectors, though very stable, are present only in a few copies in the cell.

Vectors derived from naturally occurring yeast plasmids, e.g. vectors derived from the two micron-like plasmid (two-micron vectors). Such two micron-derived plasmids occur in high copy number, their stability however is impaired when heterologous DNA is inserted.

There are several possibilities for improving the stability and for regulating the copy number of a vector. In order to achieve this goal it has been suggested to insert the CUP1 gene, coding for a metallothionein, into the vector (U.S. Pat. No. 4,935,350; R. C. A. Henderson et al., Current Genetics 9 (1985), 133–138).

Metallothioneins (MTs) are small, cysteine-rich metal binding polypeptides widely distributed among eukaryotes. *S. cerevisiae* contains normally a single MT protein that is encoded by the CUP1 gene. The CUP1 locus has been shown to confer copper resistance to yeast cells and consists of e.g. 10 or more tandemly repeated copies of the CUP1 gene. Copper resistance relies on a combination of CUP1 amplification and CUP1 transcriptional induction following the addition of exogenous copper. A cis acting upstream activation site ($UAS_c$) required for promotion of copper-inducible transcription of the CUP1 gene has been identified as well as the binding of a cellular factor to $UAS_c$. The binding factor is the product of ACE1 (=CUP2) gene which is essential for copper-induced transcription of CUP1 gene. The ACE1 protein is a transcriptional activator that binds copper ions thereby altering its conformation and activating its DNA-binding domain. The conformational change of the ACE1 protein and its binding to the $UAS_c$ eventually allows the CUP1 gene to be transcribed. An important feature of the CUP1 system is its autoregulation. This depends on the ability of the CUP1 protein (metallothionein) to bind copper ions itself. Thus, the CUP1 protein appears to repress its own synthesis by complexing free copper ions in the cells, which, in turn, interferes with ACE1 activation.

An insertion of a functional CUP1 gene and a polypeptide expression cassette into a two micron-derived plasmid surprisingly leads to enhanced stability of the two micron-derived plasmid and to amplification via an increased plasmid copy number in the presence of copper ions. This is surprising because the two micron-derived plasmid itself contains already all functions for high copy number extrachromosomal existence. The increased plasmid copy number frequently causes an improved expression of heterologous genes also present on the plasmid. It was surprisingly found, that yield in heterologous gene expression can be further increased significantly if the genuine chromosomal CUP1 genes are disrupted, or if only a single copy of the CUP1 gene, that can not be amplified, is present in the genome.

DESCRIPTION OF THE INVENTION

The present invention concerns a method for the production of a polypeptide comprising culturing in a complex culture medium a yeast strain which contains not more than one functional CUP1 gene in the genome and harbors a yeast two micron-derived plasmid comprising a functional CUP1 gene and a polypeptide expression cassette, and isolating the produced polypeptide; wherein the culture medium is supplied with a CUP1 promoter inducing amount of a copper salt.

In a preferred embodiment of the invention, the polypeptide expression cassette consists of a yeast promoter operably linked to a first DNA sequence encoding a yeast signal peptide linked in the proper reading frame to a second DNA sequence coding for a polypeptide and a DNA sequence containing yeast transcription termination signals.

The polypeptide encoded by the second DNA sequence may be homologous or heterologous to yeast. In a preferred embodiment of the invention, the expressed polypeptide is a heterologous one. These heterologous polypeptides can also be processed further, e.g. glycosylated. Useful polypeptides are, for example, enzymes which can be used, for the production of nutrients and for performing enzymatic reactions in chemistry, or polypeptides which are useful and valuable as nutrients or for the treatment of human or animal diseases or for the prevention thereof, for example hormones, polypeptides with immunomodulatory, anti-viral and anti-tumor properties, antibodies, viral antigens, vaccines, clotting factors, enzyme inhibitors, foodstuffs and the like.

Such heterologous structural genes are for example those coding for hormones such as secretin, thymosin, relaxin, calcitonin, luteinizing hormone, parathyroid hormone, adrenocorticotropin, melanoycte-stimulating hormone, β-lipotropin, urogastrone or insulin, growth factors, such as epidermal growth factor, insulin-like growth factor (IGF), e.g. IGF-I and IGF-II, mast cell growth factor, nerve growth factor, glia derived nerve cell growth factor, or transforming growth factor (TGF), such as TGFα or TGFβ, e.g. TGFβ1, β2 or β3, growth hormone, such as human or bovine growth hormones, interleukin, such as interleukin-1 or -2, human macrophage migration inhibitory factor (MIF), interferons, such as human α-interferon, for example interferon-αA, αB, αD or αF, β-interferon, γ-interferon or a hybrid interferon, for example an αA-αD- or an αB-αD-hybrid interferon, especially the hybrid interferon BDBB, proteinase inhibitors such as α₁-antitrypsin, SLPI and the like, hepatitis virus antigens, such as hepatitis B virus surface or core antigen or hepatitis A virus antigen, or hepatitis nonA-nonB antigen, plasminogen activators, such as tissue plasminogen activator or urokinase, tumour necrosis factor, somatostatin, renin, β-endorphin, immunoglobulins, such as the light and/or heavy chains of immunoglobulin D, E or G, or human-mouse hybrid immunoglobulins, immunoglobulin binding factors, such as immunoglobulin E binding factor, e.g. sCD23 and the like, calcitonin, human calcitonin-related peptide, blood clotting factors, such as factor IX or VIIIc, erythropoietin, eglin, such as eglin C, desulphatohirudin, such as desulphatohirudin variant HV1, HV2 or PA, human superoxide dismutase, viral thymidin kinase, β-lactamase, glucose isomerase. Preferred genes are those coding for a human α-interferon or hybrid interferon, particularly hybrid interferon BDBB, and most preferentially desulphatohirudin.

The term "desulphatohirudin" is intended to embrace all desulphatohirudin compounds described in literature or obtainable from a transformed microorganism strain containing DNA which codes for a desulphatohirudin. Such desulphatohirudins are, for example, desulphatohirudin variants HV1, HV2 and HV3 (PA), as well as other hirudin proteins described by M. Scharf et al. FEBS Lett. 255 (1989), 105–110. It is to be understood that hirudin derivatives having hirudin activity (i.e. having a thrombin inhibiting action) are also covered by the term "desulphatohirudin". Such derivatives are, for example, C-terminally shortened desulphatohirudins, i.e. desulphatohirudins lacking one to seven, preferably one to four, amino acids at the C-terminus, and muteins of hirudins differing from the latter by the substitution of single or plural, e.g. one to five, amino acids for the genuine amino acids. The preferred desulphatohirudin is desulphatohirudin variant HV1.

Suitable yeast strains according to the invention include strains of *Saccharomyces cerevisiae* containing the endogenous two-micron plasmid or such strains which have been cured of said endogenous two-micron plasmid (see EP-A-340 170). The yeast strains according to the invention can be devoid of the endogenous two-micron plasmid (so-called "cir⁰ strains"). Preferred yeast strains are single or multiple protease-deficient yeast strains, i.e. yeast strains lacking especially carboxypeptidase ysca and yscY proteolytic activity and, optionally additionally, protease yscA and/or yscB activity (see EP-A-341 215). The yeast strains suitable for the process according to the present invention contain not more than one functional CUP1 gene in the genome. Especially preferred yeast strains lack genomic CUP1 gene product activity. Optionally, the yeast strains according to the invention contain 1 or more additional such as 1 to 3 copies of the chromosomal ACE1 gene.

The transformed yeast strains are cultured using methods known in the art. Thus, the transformed yeast strains according to the invention are cultured in a liquid complex culture medium containing components which are essential for the yeast strain to survive and to grow, such as assimilable sources of carbon and nitrogen, inorganic salts, vitamins, growth promoting substances such as additional amino acids, sugars and the like.

Corresponding complex culture media which can be used for culturing yeast are known in the art. For examples, such culture media contain tryptone, peptone, meat extracts, malt extracts, yeast extracts, casamino acids, corn steep liquor, soy bean flour, whey, whey hydrolysate etc., and especially mixtures thereof and are optionally additionally supplemented with sugars (e.g. dextrose, glucose, sucrose, galactose etc.), vitamins (e.g. biotin), individual amino acids, inorganic salts (for example, sulphates, chlorides, phosphates and carbonates of sodium, potassium, magnesium and calcium, furthermore corresponding salts of trace elements, such as iron, zinc and manganese) and the like taking into account that all essential components as outlined above are to be present in the medium. A preferred culture medium is the commercially available medium YPD (yeast extract, peptone, dextrose; cf. Methods Enzymol. 194, 13) optionally supplemented with inorganic salts and vitamins.

The cultivation is carried out by employing conventional techniques. The culturing conditions, such as temperature, pH of the medium and fermentation time are selected in such a way that maximal levels of polypeptide are produced. A chosen yeast strain is preferably grown under aerobic conditions in submerged culture with shaking or stirring at a temperature of about 25° to 33° C., preferably at about 28° C., at a pH value of from 4 to 7, for example at approximately pH 5 to 6, and for at least 1 to 3 days, preferably 3 to 4 days, such that satisfactory yields of polypeptides are obtained. Culturing can be carried out either as a batch process, as a fed batch process, as a repeated fed batch process, or continuously.

The culture medium is supplied with a CUP1 promoter inducing amount of a copper(II) salt, particularly copper sulphate. The optimum amount of copper (the amount which provides for the maximal titers in polypeptide) depends, above all, on the genetic background of the host cell, the components of the expression vector used and the composition of the culture medium, and can be determined by the artisan applying routine tests, e.g. by "titration" (determining the polypeptide titer by HPLC as a function of the amount of copper added). A routine test has been described by T. Etcheverry (loc. cit., page 324 therein). The yeast strains according to the invention are rather insensitive to high concentrations of copper ions because the lethal concentration of copper ions is far beyond the concentration needed for optimal production and therefore can be adjusted easily. If it is desired to use the CUP1 promoter in a pseudo-constitutive manner, the culture medium is supplied, right at the time of inoculation, with the copper salt.

The polypeptide can be isolated by conventional means. For example, the first step consists usually in lysing the cell wall and removing the cell debris by centrifugation or, in the case of secretory proteins, in separating the cells from the culture fluid by means of centrifugation. The resulting supernatant can be enriched for polypeptide by treatment with polyethyleneimine so as to remove most of the non-proteinaceous material, and precipitation of the proteins by saturating the solution with ammonium sulphate. Host proteins, if present, can also be precipitated, for example, by means of acidification with acetic acid (for example 0.1%, pH 4–5). Other purification steps include, for example, desalination, chromatographic processes, such as ion exchange chromatography, gel filtration chromatography, partition chromatography, HPLC, reversed phase HPLC and the like. The separation of the constituents of the mixture is also effected by dialysis, according to charge by means of gel electrophoresis or carrier-free electrophoresis, according to molecular size by means of a suitable Sephadex column, by affinity chromatography, for example with antibodies, especially monoclonal antibodies.

In the case of desulphatohirudin, irrespective of the yeast strain, promoter and signal peptide used, the produced desulphatohirudin is predominantly (i.e. more than 90%) secreted into the culture medium. After centrifugation, thrombin, coupled to a suitable carrier for affinity chromatography can be used to separate the hirudin as well as other processes, especially those known from the literature. In general, in the case of desulphatohirudin only a few purification steps are required in order to get a desulphatohirudin product which is essentially free of contaminants.

The transformed yeast cells according to the invention can be prepared by recombinant DNA techniques comprising the steps of providing a yeast expression plasmid comprising a functional CUP1 gene and a polypeptide expression cassette, transforming a yeast strain that contains not more than one functional CUP1 gene in the genome with said yeast expression plasmid, and selecting transformed yeast cells from untransformed yeast cells.

Yeast expression plasmids

The invention concerns a yeast two micron-derived hybrid plasmid comprising the functional CUP1 gene and a polypeptide expression cassette.

Functional CUP1 genes have been cloned and extensively characterized e.g. by T. R. Butt and D. J. Ecker, Microbiol. Rev. 51 (1987), 351–364 and T. R. Butt et al. Gene 27 (1984), 23–33. They comprise e.g. the yeast CUP1 promoter (including the CUP1 UAS) operably linked to a DNA sequence coding for the metallothionein, and a DNA sequence containing yeast transcription termination signals. Most preferably a 1.3 kb BamHI fragment containing the full metallothionein encoding gene—CUP1—is isolated from plasmid YEp3362xSst (Wright, C. F. et al. Nucleic Acids Res. 14 (1986), 8489–8499) is used.

The polypeptide expression cassette comprises, for example, a yeast promoter operably linked to a DNA sequence encoding a polypeptide.

In a preferred embodiment the polypeptide expression cassette consists of a yeast promoter operably linked to a first DNA sequence encoding a yeast signal peptide linked in the proper reading frame to a second DNA sequence coding for a polypeptide, and a DNA sequence containing yeast transcription termination signals.

Preferred polypeptides are heterologous polypeptides as described above.

Suitable yeast promoters are for example any constitutive or inducible yeast promoter which can be used for the expression of polypeptides by yeast in complex media, e.g. the CUP1 promoter, the GAPDH (including shortened constitutive versions thereof, e.g. GAPFL etc.) GAL1(10), PYK, TPI, ADH and PGK promoters. Preferred promoters are the constitutive GAPFL and especially the CUP1 promoter. These promoters are well known and can be produced and used in manners known per se.

The DNA sequence of the CUP1 promoter for example is known from T. R. Butt et al., (Proc. Natl. Acad. Sci. USA 81 (1984), 3332–3336). Accordingly, the CUP1 promoter can be provided by chemical DNA synthesis or isolated from genomic *S. cerevisiae* DNA using suitable DNA probes, e.g. by polymerase chain reaction (PCR). The CUP1 promoter used in the present invention includes the transcription initiation signals and the upstream activation sequence ($UAS_c$) located at positions –105 to –148 (relative to the transcription start site of CUP1; P. First et al. Cell 55 (1988), 705–717). Preferably, use is made of existing restriction sites 5' of UAS, e.g. of the BamHI site located at position –455 of the CUP1 gene (T. R. Butt et al., supra) and of a restriction site 3' of the transcription start signals (e.g. a EcoRI site) artificially introduced by chemical synthesis or by the oligonucleotide used in PCR. The resulting restriction fragment, e.g. a 0.4 kB [Sau3A]/BamHI-EcoRI fragment, especially that contained in the construct depicted in SEQ ID NO:3, can be linked to the DNA sequence encoding a yeast signal peptide.

There are few examples in literature using an inducible CUP1 promoter for the expression of heterologous proteins by yeast (cf. T. R. Butt et al., Microbiol. Rev. 51 (1987), 351–364; T. Etcheverry, Methods Enzymol. 185 (1990), 319–329; U.S. Pat. No. 4,940,661). The methods described include culturing a transformed yeast strain harboring an expression vector with a CUP1 expression cassette in yeast minimal media containing copper ions. Chemically defined minimal media are chosen because it is generally believed that components (proteins etc.) of complex media will interact with (complex) the copper ions thus preventing ACE1 activation. The attainable cell density (OD value) and, as a consequence, the titers obtainable are correspondingly low. The latter results have so far limited the widespread application of the CUP1 promoter system in biotechnological research and production.

Surprisingly, it has now been found that, contrary to all expectations, complex yeast media can be used in connection with the copper induced CUP1 expression cassette without any deleterious effect on expression level or efficiency being observable. Furthermore, when the CUP1 promoter is used in a pseudo-constitutive manner, i.e. the culture medium is supplied with copper right at the time of inoculation, to direct the secretion of polypeptides by yeast into the culture medium, it is surprisingly found that this promoter is superior to strong constitutive yeast promoters.

Using an expression system including the CUP1 promoter, there is surprisingly no suppression by the same promoter in the whole CUP1 gene on the same vector or the metallothionein produced thereby.

The DNA sequence encoding a yeast signal peptide ("signal sequence") is preferably derived from a yeast gene coding for a polypeptide which is ordinarily secreted. Yeast signal sequences are, for example, the signal and prepro sequences of the yeast invertase (SUC2), α-factor, pheromone peptidase (KEX1), "killer toxin" and repressible acid phosphatase (PHO5) genes and the glucoamylase signal sequence from *Aspergillus awamori*. Additional sequences, such as pro- or spacer-sequences which may carry specific processing signals can also be included in the constructions to facilitate accurate processing of precursor molecules. For example, the processing signals contain a Lys-Arg residue, which is recognized by a yeast endopeptidase located in the Golgi membranes. The preferred signal sequences according to the present invention are those of the yeast PHO5 gene and of the yeast invertase gene.

The DNA sequence coding for the polypeptide, especially heterologous polypeptide, can be isolated e.g. from genomic DNA or a double-stranded DNA (ds cDNA) is produced complementary to the corresponding mRNA, or a gene coding for the amino acid sequence of the polypeptide is produced by means of chemical and enzymatic processes, in a manner known per se.

A DNA sequence containing yeast transcription termination signals is preferably the 3' flanking sequence of a yeast gene which contains proper signals for transcription termination and polyadenylation. The preferred flanking sequence is that of the yeast PHO5 gene.

The yeast promoter, the DNA sequence coding for the signal peptide, the DNA sequence coding for the polypeptide and the DNA sequence containing yeast transcription termination signals are operably linked to each other, i.e. they are juxtaposed in such a manner that their normal functions are maintained. The array is such that the yeast promoter effects proper expression of the signal sequence-polypeptide gene complex, the transcription termination signals effect proper termination of transcription and polyadenylation and the signal sequence is linked in the proper reading frame to the polypeptide gene in such a manner that the last codon of the signal sequence is directly linked to the first codon of the gene for the polypeptide. The yeast promoter is preferably joined to the signal sequence between the major mRNA start and the ATG naturally linked to the promoter gene. The signal sequence has its own ATG for translation initiation. The junction of these sequences may, for example, be effected by means of synthetic oligodeoxynucleotide linkers carrying the recognition sequence of an endonuclease. Examples for corresponding desulphatohirudin expression cassettes are described in EP-A-341 215.

Apart from the polypeptide expression cassette and the functional CUP1 gene, the expression plasmids according to the invention comprise a DNA segment originating from two-micron DNA containing the origin of replication or, if a two-micron DNA free strain of yeast is used, total two-micron DNA. The latter type of plasmids is preferred. For example, the plasmids according to the invention contain the complete two-micron DNA in an uninterrupted form, i.e. two-micron DNA is cleaved once with a restriction endonuclease, the linearized DNA is linked with the other components of the vector prior to recircularization. The restriction site is chosen such that normal function of the REP1, REP2 and FLP genes and of the ORI, STB, IR1 and IR2 sites of two-micron DNA as well as small "FLP recognition target" (FRT) sites, located near the center of each inverted repeat (IR) at which the FLP recombinase acts, is maintained. Optionally, the restriction site is chosen such that the D gene of two-micron DNA is kept intact too. Suitable restriction sites are, for example, the unique PstI site located within the D gene and the unique HpaI and SnaBI sites located outside of all of said genes and sites. However, it is likewise possible to insert the expression cassette and further components (cf. below) at different (such as two) restriction sites, especially those mentioned above, within two-micron DNA.

Such a plasmid derivative may comprise only two invertedly repeated FRT sites or an additional, third FRT site. The former kind of plasmid is hereinafter called a "symmetric two micron-like hybrid vector". The latter kind of plasmid is hereinafter called "symmetric two micron-like disintegration vector" despite it is not a real symmetric plasmid but gives rise to a symmetric two micron-like hybrid vector in the yeast cell transformed therewith.

A symmetric two micron-like hybrid vector of the invention does preferentially not contain bacterial or viral DNA sequences, i.e. DNA derived from a bacterial genome, plasmid or virus. However, a two micron-like disintegration vector of the invention may comprise DNA sequences of prokaryotic origin between the two directly repeated FRT sites which are excised from the vector in the transformed yeast cell in which the symmetric two micron-like hybrid vector is generated from the disintegration vector. These DNA sequences are bacterial sequences as described below and can provide to the vector essential structural or functional features or can also only have the function of filling up the two regions between the two invertedly repeated FRT sites of an unsymmetric two micron-like plasmid derivative or of an "unsymmetric" disintegration vector in order to construct a symmetric two micron-like hybrid vector or a symmetric disintegration vector.

In a two micron-like hybrid vector which is symmetric within the meaning of the present invention or in a disintegration vector which gives rise to such a symmetric two micron-like hybrid vector the lengths of the regions located between the two invertedly repeated FRT sites have a ratio from about 1:1 up to about 5:4, i.e. the larger region is up to about 20% larger than the smaller one.

In a preferred embodiment of invention, the two regions between invertedly repeated FRT sites of the circular form of the two-micron DNA have approximately the same length.

Preferably, the expression plasmids according to the invention include one or more, especially one or two, selective genetic markers for yeast and such a marker and (except for symmetric two-micron like hybrid vectors) an origin of replication for a bacterial host, especially *Escherichia coli*.

As to the selective gene markers for yeast, any marker gene can be used which facilitates the selection for transformants due to the phenotypic expression of the marker gene. Suitable markers for yeast are, for example, those expressing antibiotic resistance or, in the case of auxotrophic yeast mutants, genes which complement host lesions. Corresponding genes confer, for example, resistance to the antibiotics G418, hygromycin or bleomycin or provide for prototrophy in an auxotrophic yeast mutant, for example the URA3, LEU2, LYS2, HIS3 or TRP1 gene.

As the amplification of the expression plasmids is conveniently done in a prokaryote, such as *E. coli*, a prokaryote, e.g. *E. coli*, genetic marker and a prokaryote, e.g. *E. coli*, replication origin are included advantageously. These can be obtained from corresponding prokaryotic plasmids, for example *E. coli* plasmids, such as pBR322 or a pUC plasmid, for example pUC18 or pUC19, which contain both prokaryotic, e.g. *E. coli*, replication origin and genetic marker conferring resistance to antibiotics, such as ampicillin.

Apart from the polypeptide expression cassette, replication origin(s) and genetic marker(s) the expression plasmids according to the invention contain optionally additional expression cassettes, such as 1 to 3 additional polypeptide expression cassettes and/or one additional transcriptional activator ACE1 expression cassette. The additional polypeptide expression cassette(s) are identical to or different from each other and are identical to or different from the polypeptide expression cassette already present on the vector and each comprise a yeast promoter operably linked to a first DNA sequence encoding a signal peptide linked in the proper reading frame to a second DNA sequence encoding the polypeptide and a DNA sequence containing yeast transcription termination signals. A suitable yeast promoter in such an additional polypeptide-expression cassette is, for example, any constitutive or inducible yeast promoter which can be used for the expression of polypeptides by yeast in complex media, as described above. Suitable signal sequences and transcription termination signals are especially those described above. An additional ACE1 expression cassette includes its own transcriptional and translational initiation and termination signals or, in the alternative, is transcriptionally controlled by a constitutive or inducible yeast promoter different from the ACE1 promoter, such as the CUP1 or a constitutive (shortened) GAPDH promoter (e.g. GAPFL promoter). A suitable ACE1 expression cassette is, for example, contained in the *S. cerevisiae* genomic 1.7 kb EcoRV fragment (cf. P. Fürst et al. Cell 55 (1988), 705–717). The genuine ACE1 promoter therein can be replaced by another yeast promoter, e.g. the CUP1 promoter, by conventional means and methods. The direction of transcription of the additional polypeptide and/or ACE expression cassettes is not crucial and may be the same as or opposite to the direction of transcription of the polypeptide-expression cassette already present in the vectors of the invention.

The invention concerns also a method for the preparation of the novel expression plasmids as defined above. The expression plasmids according to the invention are prepared by methods known in the art, for example by linking the polypeptide expression cassette, the CUP1 gene, the DNA fragments containing selective genetic markers for yeast and optionally for a bacterial host, the origins of replication for yeast and optionally for a bacterial host, and the optionally additional polypeptide and/or ACE1 expression cassettes in the predetermined order using conventional chemical or biological in vitro synthesis procedures. Preferentially the plasmids are constructed and prepared using recombinant DNA techniques. For the preparation by recombinant DNA techniques suitable DNA fragments are ligated in vitro in conventional manner. The ligation mixture is then transformed into a suitable prokaryotic or eukaryotic host depending on the nature of the regulatory elements used, and a transformant containing the desired vector is selected according to conventional procedures. The plasmids can be multiplicated by means of the transformed hosts and can be isolated in conventional manner. The choice of the host depends on the regulatory sequences located on the vector. As the expression vectors of the invention preferentially comprise regulatory sequences functional in prokaryotes, e.g. *E. coli*, a prokaryotic host, e.g. *E. coli*, is preferred for the construction and multiplication of the vector.

Transformed yeast strains

The invention concerns furthermore a yeast strain which contains not more than one functional CUP1 gene in the genome and harbors a yeast hybrid plasmid comprising a polypeptide expression cassette and the functional CUP1 gene, and a method for the production thereof.

The transformation of yeast with the hybrid plasmids according to the invention may be accomplished according to methods known in the art.

Preferred yeast strains are those mentioned above, e.g. strains of *S. cerevisiae* which have been cured of the endogenous two-micron plasmid ("cir⁰ strains") and especially strains which are singly or multiply deficient in yeast proteases, such as carboxypeptidases yscα and yscY. Further preferred yeast strains lack genomic CUP1 gene product activity. Methods for the production of such yeast strains are described, for example, in EP-A-340 170 and EP-A-341 215. Yeast strains which lack genomic CUP1 gene product activity or contain not more than one functional CUP1 gene in the genome are known or can be prepared in a manner known per se, for example by site-directed mutagenesis or gene-disruption or gene replacement (cf. H. Rudolph et al., Gene, 36 (1985), 87–95). As the sequence of the chromosomal CUP1 gene is known the latter can be made defective by insertion, substitution or deletion making use of the well-known site directed mutagenesis procedure (see, for example, M. J. Zoller and M. Smith Methods Enzymol. 100 (1983), 468) which involves the preparation of an appropriately devised mutagenic oligodeoxyribonucleotide primer. Alternatively, the genomic CUP1 gene can be replaced by foreign DNA or said foreign DNA can be inserted into a suitable restriction site of the CUP1 gene. For example, in order to prepare a yeast mutant deficient in the chromosomal CUP1 genes foreign DNA is inserted into a suitable restriction site occurring in the CUP1 genes. In case the yeast strain used has a defect in a chromosomal gene coding for an enzyme of amino acid or purine (e.g. uracil) biosynthesis a corresponding intact gene (such as URA3) can be inserted into the chromosomal CUP1 genes thus providing for prototrophy in the auxotrophic yeast strain and changing the genotype at the same time from CUP1 to cup1. The gene replacement or directed mutagenesis procedures are commonly applied in the art and are absolutely reproducible.

A further current method to create yeast strains having a desired genetic background, for example having chromosomal CUP1 genes disrupted and/or having deficiencies in certain proteases, consists in meiotic crossing of suitable yeast strains and subsequent tetrad analysis. The tetrads, which derive from the diploid cells, are dissected according to standard genetic techniques. Random assortment among the four spores of a tetrad allows the construction of suitable mutants in subsequent crosses. Random spore analysis can also be used as an alternative system.

Yeast strains containing 1–3 additional copies of the chromosomal ACE1 gene can also be prepared in a conventional manner. For example, the ACE1 gene(s) can be inserted into appropriate restriction site(s) of chromosomal gene(s) conferring antibiotic resistance or in gene(s) involved in amino acid or purine or pyrimidine base synthesis rendering resulting yeast strains containing such additional copy (copies) of the ACE1 gene antibiotic sensitive and, respectively, auxotrophic with respect to the corresponding amino acid, purine or pyrimidine base.

BRIEF DESCRIPTION OF THE DRAWINGS

In the following experimental part various embodiments of the present invention are described with reference to the accompanying drawings in which.

Figure 1:
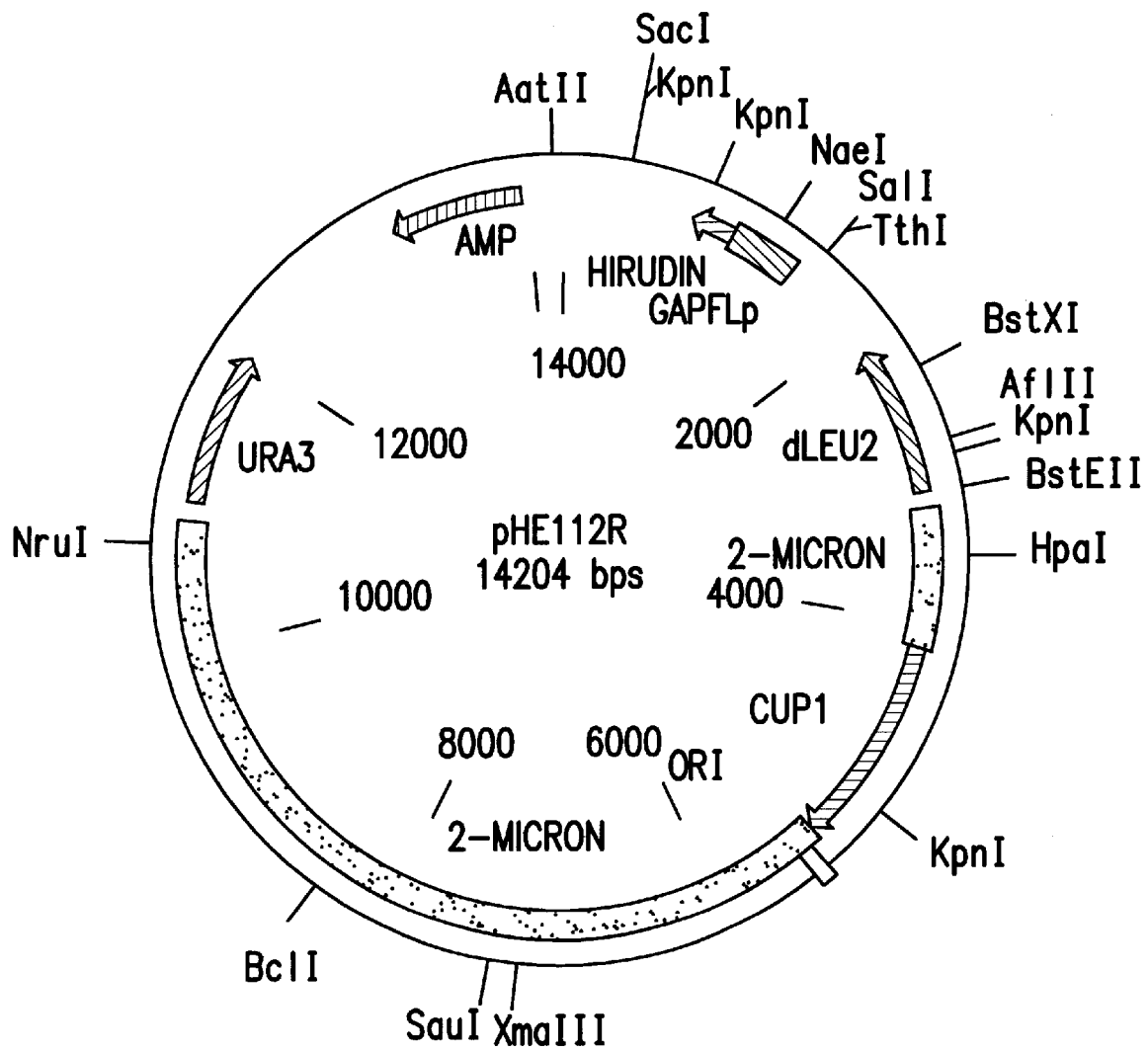
FIG. 1 is a schematic illustration of plasmid pHE112R.

The following abbreviations are used in the figures:
term=PHO5 transcription terminator;
p in CUP1p, GAPFLp and ACE1p=promoter.

The following examples illustrate the invention and should not be construed as a limitation thereof.

Experimental Part

Strains and plasmids

*E. coli* DH5αF': *Escherichia coli* K12 F' endA1 hsdR17(r⁻ m⁺) supE44 thi1 recA1 pyrA relA1 PHI801acZdelM15 del(lacZYA-argF)U169; Hanahan D (1983) Studies on transformation of *Escherichia coli* with plasmids. J. Mol. Biol. 166:557 (Bethesda Research Laboratories).

*S. cerevisiae* H449: *Saccharomyces cerevisiae* MATa, ura3Δ5, leu2-3, leu2-112, prb1, cps1, [cir⁰]. DSM 4413; Feb. 18, 1988.

*S. cerevisiae* HT462/TH3: MATα, cup1::URA3, kex1, prc1, leu2-3; leu2-212; DSM 7190; Jul. 22, 1992.

*S. cerevisiae* strain 55.6B; MATa, his3, leu2, trp1, ura3-52, cup1::URA3; cf. Thiele, D. J. et al. Science 231 (1986), 854–856

Plasmid YEp3362xSst: Wright, C. F. et al. Nucleic Acids Res. 14 (1986), 8489–8499.

Plasmid pDP34: EP-A-340 170, FIG. 3 therein; a yeast-*E. coli* shuttle vector with the ampicillin resistance marker for *E. coli* and the URA3 and dLEU2 yeast selective markers. It contains the complete 2micron sequence in the A form and is REP1, REP2 and FLP proficient. DSM 4473; Mar. 14, 1988.

Plasmid pJDB207/GAPFL-YHIR: A yeast plasmid for the expression of desulphatohirudin variant HV1 under the control of a short, constitutive promoter of the yeast glyceraldehyde-3-phosphate dehydrogenase (GAPDH) gene. The coding sequence of desulphato-hirudin consists of preferred yeast codons; cf. EP-A-340 170

Plasmid pTZ18R: Plasmid derived from pUC 18 includes an M13 origin of replication so it can become single stranded and be packaged in M13 phage heads with the aid of a helper M13 phage. Mead DA, Szczesna-Skorupa E, Kemper B, Single stranded DNA 'blue' T7 promoter plasmids: a versatile tandem promoter system for cloning and protein engineering. Protein Engineering 1 (1986), 67–74. (Pharmacia).

Plasmid pFBY2: This plasmid is constructed by inserting the 166 bp AluI fragment containing the FRT site from S. cerevisiae two micron plasmid between the HindIII and EcoRI sites of pTZ18R and the whole of the two micron plasmid cut with XbaI into the unique XbaI site of pTZ18R. DSM 6271; Dec. 14, 1990.

Plasmid pFBY4: This plasmid consists of a 1.1 kb XbaI fragment containing the whole of the URA3 gene of S. cerevisiae cloned into the unique XbaI site of pTZ18R. This plasmid serves as a convenient source for a 1.1 kb URA containing XbaI fragment. DSM 6272; Dec. 14, 1990.

Plasmid pFBY5: pFBY5 is derived from a large plasmid containing the whole of the S. cerevisiae two micron plasmid plus the URA3 and Leu2 genes of S. cerevisiae in the bacterial vector pUC18. Into the unique SalI site of this vector is inserted a 1.1 kbp SalI fragment containing an expression cassette consisting of a promoter derived from the S. cerevisiae GAPDH gene fused to the PHO5 signal sequence which in turn is fused to a synthetic hirudin encoding DNA fragment, which is followed by the PHO5 terminator. DSM 6273; Dec. 14, 1990.

Plasmid pFBY29: This plasmid consists of a 2 kbp BamHI/SalI fragment containing the LEU2 gene. The fragment is inserted between the BamHI and SalI sites of pTZ18R. pFBY29 serves as a source of a 2.0 kbp fragment containing LEU2. DSM 6275; Dec. 14, 1990.

All DNA manipulations are—if not otherwise noted—carried out according to standard protocols (e.g. Maniatis, T. et al.: Molecular cloning: a laboratory manual. Cold Spring Harbor Laboratory, Cold Spring Harbor, N.Y. (1982).

EXAMPLE 1

Construction of plasmid pHE 112R. A 2micron plasmid containing the GAPFLp-hirudin expression cassette and the full CUP1 gene To enhance plasmid stability and increase plasmid copy number a 1.3 kb fragment containing the full-length CUP1 gene is inserted into plasmid pDP34/GAPFL-YHIR, a plasmid which is designed for the expression of desulphatohirudin variant HV1 under the control of a short, constitutive promoter of the yeast glyceraldehyde-3-phosphate dehydrogenase (GAPDH) gene (GAPFLp).

For the construction of pDP34/GAPFL-YHIR pDP34 is used as starting plasmid. pDP34 (cf. EP-A-340 170, FIG. 3 therein) is a yeast-E. coli shuttle vector with the ampicillin resistance marker for E. coli and the URA3 and dLEU2 yeast selective markers. It contains the complete 2micron sequence in the A form and is REP1, REP2 and FLP proficient. Plasmid pDP34 is digested with BamHI. The sticky ends of the restriction site are filled in a reaction with Klenow DNA polymerase (T. Maniatis et al., in: "Molecular Cloning. A Laboratory Manual", Cold Spring Harbor Laboratory, 1982). The DNA is further cut with SalI and the 11.8 kb vector fragment is isolated on a preparative 0.6% agarose gel. The DNA is recovered by electroelution and ethanol precipitation.

Plasmid pJDB207/GAPFL-YHIR (cf. EP-A-340 170) is digested with HindIII. The sticky ends are converted to blunt ends by Klenow DNA polymerase. The DNA is ethanol precipitated and further digested with SalI. The 1.1 kb SalI-[HindIII]/blunt end fragment contains the complete expression cassette with pBR322 sequences, the GAPFL promoter, the PHO5 signal sequence fused in frame to the coding sequence of desulphatohirudin and the PHO5 transcription termination fragment. The 1.1 kb fragment is isolated on a preparative 0.8% agarose gel, recovered from the gel by electroelution and purified by DE52 ion exchange chromatography and ethanol precipitation.

0.2 pmoles of the 1.1 kb fragment and 0.1 pmoles of the 11.8 kb vector fragment are ligated in 10 µl of 60 mM Tris-HCl pH 7.5, 10 mM $MgCl_2$, 5 mM DTT, 3.5 mM ATP and 400 units of T4 DNA ligase for 16 h at 15° C. A one µl aliquot is used to transform E. coli HB101 $Ca^{2+}$ cells. 5 transformed, ampicillin resistant colonies are analyzed. Plasmid DNA is digested with BamHI and SalI/BamHI. One clone with the correct restriction fragments is selected and referred to as pDP34/GAPFL-YHIR (for details, see EP-A-340 170).

A 1.3 kb BamHI fragment containing the full metallothionein encoding gene—CUP1—is isolated from plasmid YEp3362xSst (Wright, C. F. et al. Nucleic Acids Res. 14 (1986), 8489–8499). YEp3362xSst is digested with BamHI, the 1.3 kb fragment isolated, purified and ligated with BamHI cut pUC19. The resulting plasmid is named pHE105. The 1311 bp BamHI fragment, containing the CUP1 promoter, the CUP1 encoded metallothionein open reading frame (ORF) and the CUP1 terminator is shown in SEQ ID NO:1.

pHE105 is digested with BamHI, the 1.3 kb CUP1 containing fragment is isolated and the sticky ends converted to blunt ends by Klenow DNA polymerase. pDP34/GAPFL-YHIR is digested with SnaBI, the cut plasmid is purified and the blunt ends are dephosphorylated by alkaline phosphatase treatment. The 1.3 kb [BamHI]/blunt end fragment containing CUP1 is ligated into SnaBI-cut pDP34/GAPFL-YHIR. E. coli is transformed with the resulting plasmid pHE112R. pHE112R is tested for orientation of the metallothionein ORF by digestion with KpnI. The metallothionein ORF is contained in pHE112R in a anti-clockwise orientation with respect to the GAPFL-hirudin expression cassette. pHE112R is shown in FIG. 1.

EXAMPLE 2

Construction of plasmid pPFY56. A hybrid gene containing the CUP1 promoter, the PHO5 leader sequence and a synthetic hirudin gene In order to achieve inducible, high level expression of secreted desulphato-hirudin, DNA sequences coding for hirudin and for the PHO5 leader sequence are fused and placed under the control of the copper inducible CUP1 promoter. The synthetic hirudin gene, fused to the PHO5 leader sequence, is isolated from the plasmid pDP34/GAPFL-YHIR (supra) as a 0.5 kb EcoR 1 fragment that also contains PHO5 transcription termination sequences.

The CUP1 promoter (T. R. Butt et al. Proc. Natl. Acad. Sci. USA 81 (1984), 3332–3336) is cloned from S. cerevisiae genomic DNA by polymerase chain reaction(PCR) using the PCR kit from Perkin Elmer and the following two oligonucleotides as primers:

5'-GGATCCATTACCGACATTTGGGCGCTAT    SEQ ID NO:5
5'-GAATTCACAGTTTGTTTTTCTTAATATCTA  SEQ ID NO:6

100 ng of yeast genomic DNA (isolated from yeast strain H449) is incubated in 0.1 ml with 2.5 units of Taq DNA-polymerase, 0.02 mM of each primer and 0.2 mM of dATP, dCTP, TTP and dGTP in 10 mM TRIS pH 8.3, 50 mM KCl, 1.5 mM $MgCl_2$. The reaction is incubated for 30 cycles:30 sec at 92° C., for 1 min at 42° C. and at 72° C. for 1 min.

The CUP1 promoter fragment of 0.4 kb, after isolation, purification and restriction with BamHI and EcoRI, is inserted into BamHI and EcoRI cut pBR322. The resulting plasmid pBR322-CUP1 is restricted with EcoRI. The 4.4 kb vector containing the CUP1 promoter is isolated, purified and ligated with the 0.5 kb hirudin fragment. E. coli HB101 is transformed with the resulting plasmid pPFY53. pPFY53 is tested for proper orientation of the hirudin fragment by digestion with SalI. The 1082 bp BamHI/SalI fragment containing the CUP1 promoter, the PHO5 leader sequence, the hirudin gene and the PHO5 terminator is shown in SEQ ID NO:3.

Figure 2:
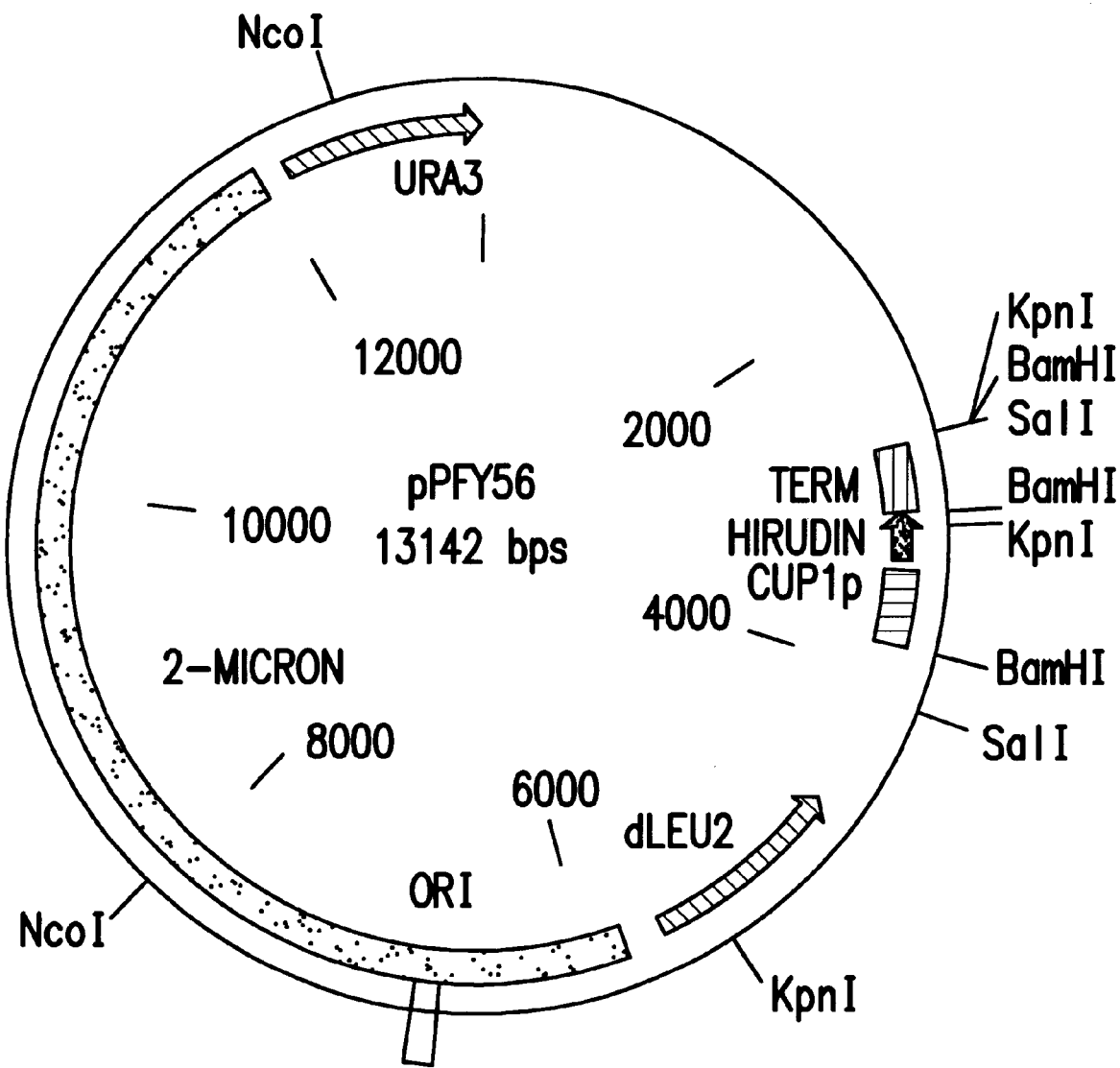
FIG. 2 is a schematic illustration of plasmid pPFY56.

The CUP1-hirudin expression cassette is isolated from pPFY53 as a 1.1 kb SalI fragment. This fragment is then inserted into SalI linearized pDP34 (supra). E. coli HB101 is transformed with the resulting plasmid pPFY56. The transformed E. coli strain is designated E. coli/PFY56. pPFY56 is shown in FIG. 2.

EXAMPLE 3

Figure 3:
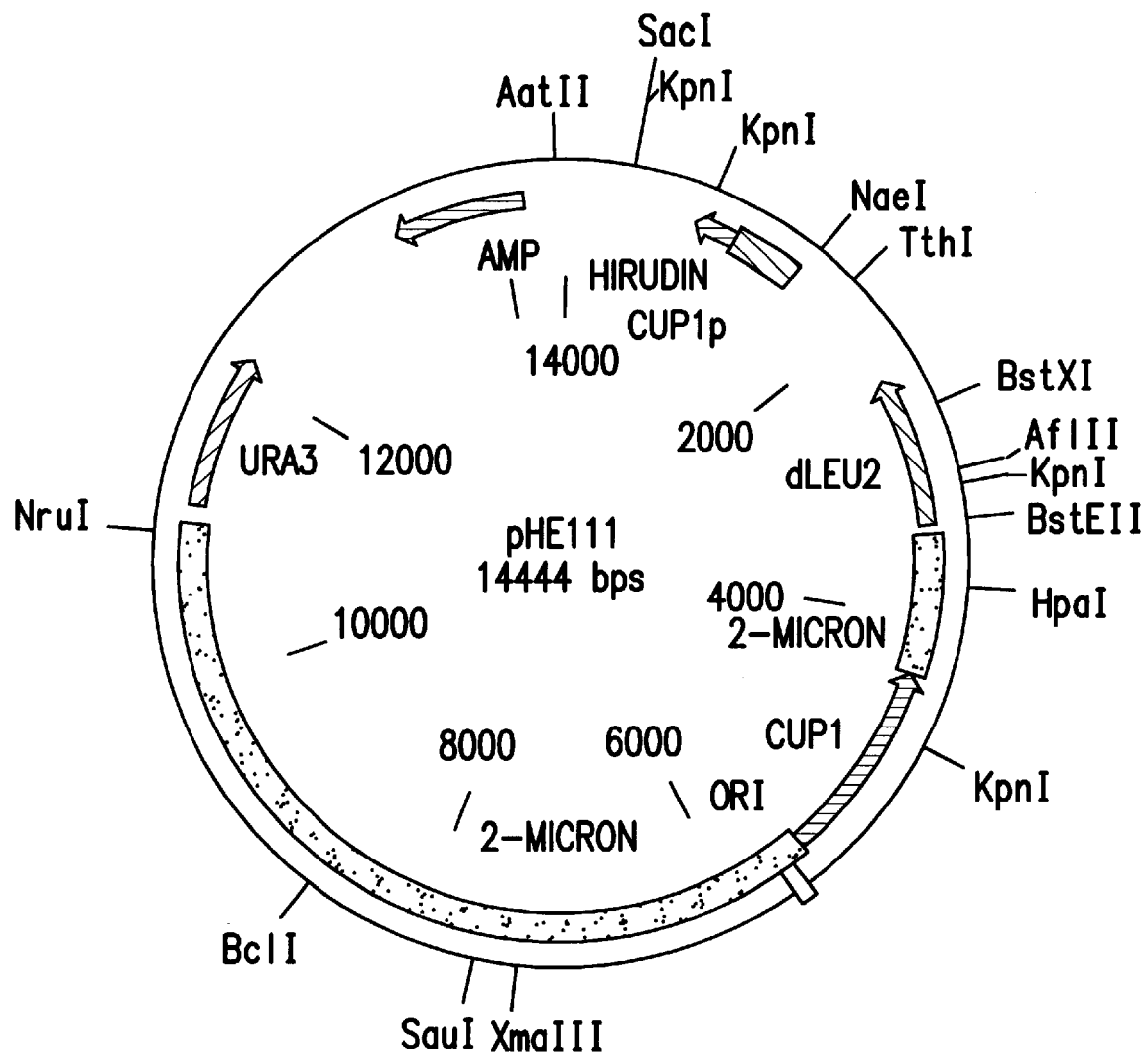
FIG. 3 is a schematic illustration of plasmid pHE111.

Construction of plasmid pHE111. A 2micron plasmid containing the CUP1p-hirudin expression cassette and the full-length CUP1 gene pPFY56 is digested with SnaBI, the cut plasmid is purified and the blunt ends are dephosphorylated by alkaline phosphatase treatment. The 1.3 kb [BamHI]/blunt end fragment containing CUP1 (Example 1) is ligated into SnaBI-cut pPFY56. E. coli HB101 is transformed with the resulting plasmid pHE111. pHE111 is tested for orientation of the metallothionein ORF by digestion with KpnI. The metallothionein ORF is contained in pHE111 in a clockwise orientation with respect to the CUP1p-hirudin expression cassette. pHE111 is shown in FIG. 3.

EXAMPLE 4

Construction of Saccharomyces cerevisiae strain TR1456

Saccharomyces cerevisiae strain TR1456 is constructed as disclosed in EP-A-341 215. Starting with Saccharomyces cerevisiae strain H449, in two subsequent series of experiments the two carboxypeptidases yscα and yscY are removed from strain H449 by disruption of their encoding genes KEX1 and PRC1, respectively. First, the gene encoding yscα, KEX1, is disrupted. For this purpose, strain H449 is transformed with a DNA fragment encoding the KEX1 gene, with the full URA3 gene inserted in the middle of the KEX1 coding region. Uracil prototrophic transformants are selected and tested for the absence of yscα activity. Next, the URA3 gene inserted at the KEX1 locus is disrupted by transformation with a plasmid containing a disrupted version of the URA3 gene, ura3Δ5 (see EP-A-341 215). Transformants which are uracil auxotrophic are selected and in the following step disrupted in their endogenous PRC1 gene coding for the carboxypeptidase yscY. The experiment is carried out in a totally analogous manner as described for the disruption of KEX1. The finally resulting isogenic derivative of strain H449 is called TR1456 and has the following genotype:

TR1456=MATa, leu2-3,112, ura3, prb1, kex1::ura3, prc1::ura3, [cir⁰]

EXAMPLE 5

Construction of a copper-resistant isogenic derivative of Saccharomyces cerevisiae strain TR1456

Saccharomyces cerevisiae strain TR1456 is—as most laboratory yeast strains—a strain which is moderately resistant to the addition of copper to the medium. This resistance is due to the presence of a 2 kb segment of chromosomal DNA which contains 2 copies of the CUP1 gene arranged as a tandem (Hamer, D. et al. Science 228 (1985), 685–690). In the presence of large amounts of copper in the medium, even higher resistant derivatives are obtained which are due to tandem reiteration of the above mentioned 2 kb CUP1-containing chromosomal DNA segment. To construct such a higher resistant derivative, S. cerevisiae TR1456 is inoculated into the synthetic minimal medium as disclosed in Example 6, supplemented with 1.2 mM copper sulphate. The culture is grown for 8 days at 30° C. and 180 r.p.m. The culture is then plated out on synthetic minimal medium without copper addition at a suitable density to obtain single colonies. DNA from selected individual colonies is prepared, digested with EcoR1, separated on agarose gels and analyzed for the presence and length of the CUP1 locus by Southern blotting. Experimental conditions are according to Hamer et al. [see above]. One colony with a shift in the electrophoretic mobility of the CUP1 locus indicative for the presence of at least 10 copies of the CUP1 locus is selected and referred to as S. cerevisiae strain TR1631.

EXAMPLE 6

Crossing of S. cerevisiae strain 55.6B (cup1::URA3) with S. cerevisiae strain TR1456 and analysis of the spores with respect to copper sensitivity The S. cerevisiae strain 55.6B (MATa, his3, leu2, trp1, ura3-52, cup1::URA3; cf. Thiele, D. J. et al. Science 231 (1986), 854–856) that is deleted in the CUP1 locus is crossed with strain TR1456 (MATa leu2-3,212, ura3Δ5, kex1, prb1, prc1) that carries approximately 3 copies of the CUP1 locus (i.e. 6 copies of the tandemly arranged CUP1 gene). Diploid heterozygous cells of the genotype cup1::URA3/CUP1 are isolated from this cross. The tetrads which are derived from the diploid cells are dissected according to standard genetic techniques [Methods in Yeast Genetics 1986 (Sherman F., Fink G. R., Hicks J. B., eds.) Cold Spring Harbor Laboratory, N.Y.]. The descendants of the four spores of every tetrad are tested for their ability to grow on YPD agar plates (10 g yeast extract, 20 g peptone, 20 g glucose and 25 g agar per liter of double distilled water) supplemented with either 0 μM, 250 μM, 500 μM or 1 mM copper sulphate. Spores that inherit the intact CUP1 gene give rise to progeny that grows vigorously on copper agar, whereas spores that inherit the disrupted cup1::URA3 gene give rise to progeny that grows poorly on copper agar. The descendents of two copper sensitive spores of several complete tetrads are tested for their ability to mate with strain TR1456. The descendents of a spore of the appropriate mating type are crossed with TR1456 and diploid heterozygous cells of the genotype cup1::URA3/CUP1 are isolated from this cross. The tetrads which are derived from the diploid cells are dissected and the spores are tested for sensitivity to copper sulphate as described above. The copper sensitive colonies obtained from approximately 50 complete tetrads are tested for growth on SD agar (6.7 g Bacto Yeast Nitrogen Base without amino acids, 20 g glucose and 25 g agar per liter of water), and on SD agar supplemented with 200 μM leucine. Colonies that do not grow on the SD plates but that do grow on SD agar supplemented with 200 μM leucine have the genotype cup1::URA3, HIS3, TRP1, leu2-3,212 and are selected for further work.

EXAMPLE 7

Classification of confirmed cup1::URA3 mutants on additional deficiency of protease yscY and protease yscα

*S. cerevisiae* cup1::URA3 mutants obtained as disclosed under example 6 are further classified with regard to the deficiency of proteases encoded by the KEX1 and PRC1 genes. Colonies deficient in the KEX1 gene are identified on the basis of their reduced ability to secrete α-factor. A detailed description of the procedure used to discriminate between colonies carrying a wild type KEX1 gene and colonies mutated in the kex1 gene can be found in EP-A-341 215, example 1 therein. Colonies deficient in the PRC1 gene are identified by means of a biochemical test that measures the proteolytic activity of the product of the PRC1 gene, namely protease yscY. This test has been described in EP-A-341 215. A single colony of the genotype cup1::URA3, kex1, prc1, leu2-3,212 is picked and is referred to as *Saccharomyces cerevisiae* HT462/TH3.

EXAMPLE 8

Transformation of strains TR1456, TR1631 and HT462/TH3 with plasmids pDP34/GAPFL-YHIR, pHE111, pHE112R and pPFY56

The plasmids pPFY56, pDP34/GAPFL-YHIR, pHE111 and pHE112R are introduced into the host strains TR1456, TR1631 and HT462 using the transformation protocol described by Hinnen et al. (Proc. Natl. Acad. Sci. USA 75 (1978), 1929). Further details of the procedure are described in EP-A-341 215. Transformed yeast cells are selected on yeast minimal media, supplemented with an optimal concentration (strain TR1456, 1631) or suboptimal concentration (strain HT462) of leucine. Single transformed yeast clones are isolated and are referred to as:

*Saccharomyces cerevisiae* TR1456/pDP34/GAPFL-YHIR
*Saccharomyces cerevisiae* TR1456/pPFY56
*Saccharomyces cerevisiae* HT462/pDP34/GAPFL-YHIR
*Saccharomyces cerevisiae* HT462/pPFY56
*Saccharomyces cerevisiae* HT462/pHE111
*Saccharomyces cerevisiae* HT462/pHE112R
*Saccharomyces cerevisiae* TR1631/pDP34/GAPFL-YHIR
*Saccharomyces cerevisiae* TR1631/pPFY56

EXAMPLE 9

Desulphato-hirudin production by strain HT462 transformed with plasmid pDP34/GAPFL-YHIR, or pPFY56, or pHE111, or pHE112R and grown in shake flasks in complex medium Cells of *Saccharomyces cerevisiae* HT462/pDP34/GAPFL-YHIR, or HT462/pPFY56, or HT462/pHE111, or HT462/pHE112R are each grown in two subsequent precultures in 20 ml synthetic medium composed of (g/l):

| | |
|---|---|
| Difco Yeast Nitrogen Base (without amino acids) | 6.7 |
| L-asparagine | 10 |
| L-histidine | 1 |
| glucose | 20 |
| L-leucine | 0.02 |

The pH of the medium is adjusted to 5.8. The first preculture is grown for 60 h at 28° C. and 180 r.p.m.. The second preculture is inoculated with 2% (volume per volume) of the first preculture and incubated for 24 h at 28° C. and 180 r.p.m.

The medium of the main culture is composed of (g/l):

| | |
|---|---|
| peptone | 5 |
| yeast extract | 10 |
| glucose | 20 |
| sucrose | 40 |
| ammonium sulphate | 3 |
| potassium dihydrogenphosphate | 2 |
| magnesium sulphate heptahydrate | 0.5 |
| sodium chloride | 0.1 |
| calcium chloride | 0.1 |
| biotin | $10^{-5}$ |

The main culture (100 ml medium) is inoculated with about $10^6$ cells/ml and incubated for 72 h at 28° C. and 180 r.p.m.. Immediately following the inoculation, sterile copper sulphate at the desired concentrations is added. At the end of the fermentation aliquots of the cultures are taken, the cells are removed by centrifugation and the culture supernatant is analyzed for desulphato-hirudin as disclosed in EP-A-340 170. The results are shown in the following Table 1.

TABLE 1

Desulphato-hirudin production by strain HT462 transformed with multicopy plasmids either containing (plasmids pHE111 and pHE112R) or lacking (plasmids pDP34/GAPFL-YHIR and pPFY56) a functional copy of the yeast metallothionein (CUP1) gene.

Desulphato-hirudin secretion (mg/l)

| plasmid | Copper sulphate concentration (μM) | | | | | | | | | | | | | |
|---|---|---|---|---|---|---|---|---|---|---|---|---|---|---|
| | 0 | 20 | 50 | 100 | 500 | 1000 | 2000 | 3000 | 4000 | 5000 | 6000 | 7000 | 8000 | 10000 |
| pDP34-GAPFL-YHir | 75 | 73 | 73 | 66 | 41 | 8 | 0 | 0 | 0 | 0 | 0 | 0 | 0 | 0 |
| pPFY56 | 99 | 103 | 104 | 107 | 34 | 3 | 0 | 0 | 0 | 0 | 0 | 0 | 0 | 0 |
| pHE112R | 80 | 72 | 109 | 115 | 137 | 150 | 168 | 184 | 191 | 177 | 160 | 137 | 132 | 110 |
| pHE111 | 12 | n.d. | n.d. | n.d. | 182 | 228 | 271 | 261 | 240 | 222 | 202 | 179 | 160 | 90 |

EXAMPLE 10

Mitotic stability of plasmids pHE111 and pHE112R during growth of strains HT462/pHE111 and HT462/pHE112R on complex medium supplied with various copper concentrations Cells of *Saccharomyces cerevisiae* HT462/pHE111 and *Saccharomyces cerevisiae* HT462/pHE112R are each grown in two subsequent precultures in 20 ml synthetic medium as described in Example 9. They are then transferred to the complex medium described in Example 9 at an initial cell density of about $10^6$ cells/ml. After 72 h incubation at 28° C. and 180 r.p.m., the cultures are diluted with a sterile solution of NaCl (9 g/l of water), and an appropriate volume is plated onto YPD-agar (10 g yeast extract, 10 g peptone, 20 g glucose, 30 g agar in 1 l of water). The colonies obtained are replica-plated onto YPD-agar supplemented with 2 mM copper sulphate. Colonies derived from a plasmid-containing cell are able to grow on this substrate, whereas colonies derived from a cell that has lost the plasmid will die. Therefore, the percentage of plasmid-containing cells can be calculated by comparing the number of colonies on agar with or without 2 mM copper sulphate. The results are shown in the following Table 2:

TABLE 2

Mitotic stability of plasmids pHE111 and pHE112R in the absence (no copper sulphate) or presence (20-4000 µM copper sulphate) of selective pressure
Plasmid-bearing cells (%)

| | Copper sulphate in the medium (µM) | | | | | |
|---|---|---|---|---|---|---|
| Strain/plasmid | 0 | 20 | 100 | 500 | 1000 | 2000 | 4000 |
| HT462/pHE111 | 47 | 54 | 65 | 89 | 96 | n.d. | 100 |
| HT462/pHE112R | 95 | n.d. | 94 | n.d. | 100 | 100 | 100 |

EXAMPLE 11

Desulphato-hirudin production by strains TR1456 and TR1631 transformed with plasmid pDP34/GAPFL-YHIR or pPFY56 and grown in shake flasks on complex medium Cells of *Saccharomyces cerevisiae* TR1456 (containing approximately six chromosomal copies of the CUP1 gene), or TR1631 (containing approximately 20 CUP1 copies) are transformed with plasmids pPFY56 or pDP34/GAPFL-YHIR as described above. Also, strain HT462/TH3 is transformed with pHE111. The transformed strains are each grown in two subsequent precultures in minimal medium, followed by a main culture in complex medium as described in example 9. Immediately following the inoculation of the main culture, sterile copper sulphate at the desired concentrations is added. At the end of the fermentation, aliquots of the cultures are taken, the cells are removed by centrifugation and the culture supernatant is analyzed for desulphato-hirudin (as disclosed in EP-A-340 170). The results are shown in the following Table 3:

TABLE 3

Comparison of transformed strain TR1631 with transformed strain TR1456
Desulphato-hirudin (mg/l)

| | Concentration of copper sulphate (mM) | | | | |
|---|---|---|---|---|---|
| Strain/plasmid | 0 | 0.5 | 1 | 2 | 4 |
| TR1631/pPFY56 | 7 | 115 | 165 | 154 | 83 |
| TR1631/pDP34/GAPFL-YHIR | 105 | n.d. | n.d. | n.d. | n.d. |
| TR1456/pPFY56 | 5 | 184 | 239 | 87 | 39 |
| TR1456/pDP34/GAPFL/YHIR | 109 | n.d. | n.d. | n.d. | n.d. |
| HT462/pHE111 | 12 | 182 | 228 | 271 | 261 |

The results show inferior productivity of a CUP1-YHIR (but not a GAPFL-YHIR) cassette when the yeast metallothionein protein is overexpressed from multiple chromosomal copies (TR1631). In contrast, expression of yeast metallothionein from a multi copy plasmid (as in strain HT462/pHE111) increases the yield of hirudin. Whilst integration of CUP1 in the expression plasmid gives higher hirudin yields, overexpression of CUP1 from the chromosome actually reduces the titers.

A copy of CUP1 integrated into the expression plasmid also results in a much broader range of copper concentrations at which good productivity can be achieved (Tables 1 and 3).

EXAMPLE 12

Construction of pFBY23

2 µg of pFBY2 is cleaved to completion by FspI in CA buffer (20 mM Tris(hydroxymethyl)aminomethane; 7 mM $MgCl_2$; 5 mM dithiothreitol; 100 mM KCl; HCl to pH 7.5). The restriction endonuclease is inactivated by heating at 65° C. for 10 min. The volume is doubled by the addition of water and the DNA fragments are blunt ended with 1 unit of T4 polymerase in the presence of 0.05 mM each of dATP, dCTP, dGTP and dTTP for 30 min at 37° C. The enzyme is heat inactivated at 65° C. for 10 min. After ethanol precipitation the DNA is recut with HindIII and EcoRI. These fragments are separated on a 2% LGT gel (Low gelling temperature agarose) in TAE buffer (40 mM Tris (hydroxymethyl)aminomethane; 2 mM Ethylenediaminetetraacetic acid (disodium salt) Acetic acid to pH 7.6). The 170 bp and the 523 bp fragments are cut out and the DNAs are purified by ElutipD chromatography.

2 µg of pTZ18R is cleaved to completion by EcoRI and HindIII in CA buffer. These fragments are separated on a 0.8% LGT gel in TAE buffer. The 2.8 kbp band is cut out and the DNA is purified by ElutipD chromatography.

Approximately 20 ng of each of the prepared fragments are ligated together with 10 pM of an unphosphorylated BamHI linker of the sequence GGGATCCC and 1 mM ATP and ligation buffer by 0.5 units of T4 ligase for 3 h at room temperature.

This ligation mixture is used to transform 40 µl of competent *E. coli* DH5αF' cells and plated on 2YT plates (16 g Tryptone; 10 g Yeast extract; 10 g NaCl per liter $H_2O$) containing ampicillin, Xgal and IPTG. To verify pFBY23, whites colonies are picked after 16 h incubation at 37° C. and miniscreened using EcoRI HindIII double digest to confirm the presence of the correct insert and a HindIII/BamHI double digest to show the BamHI linker in the previous FspI site.

EXAMPLE 13

Construction of pFBY24

2 μg of pFBY23 is cleaved to completion by HindIII and EcoRI in CA buffer. Theses fragment are separated on a 0.8% LGT gel in TAE buffer. The 701 bp band is cut out and the DNA is purified by ElutipD chromatography.

2 μg of pFBY2 is cleaved to completion by HindIII and PstI in CA buffer. These fragments are separated on a 0.8% LGT gel in TAE buffer. The 3.8 kbp fragment is cut out and the DNA is purified by ElutipD chromatography.

2 μg of pFBY2 is cleaved to completion by PstI and XbaI in CA buffer. These fragments are separated on a 0.8% LGT gel in TAE buffer. The 1.95 kbp fragment is cut out and the DNA is purified by ElutipD chromatography.

2 μg of pFBY2 is cleaved to completion by XbaI and EcoRI in CA buffer. These fragments are separated on a 0.8% LGT gel in TAE buffer. The 2.9 kbp fragment is cut out and the DNA is purified by ElutipD chromatography.

Approximately 20 ng of each of the prepared fragments are ligated together in the presence of 1 mM ATP and ligation buffer by 0.5 units of T4 ligase for 3 h at room temperature.

This ligation mixture is used to transform 40 μl of competent *E. coli* DH5αF' cells and plated on 2YT plates containing ampicillin, Xgal and IPTG. After 16 h incubation at 37° C., white colonies are picked and miniscreened using HindIII EcoRI and PstI XbaI double digests to confirm the presence of the correct inserts and BamHI to show the presence of the new BamHI site.

pFBY24 is identical to pFBY2 with the complete sequences of the plasmids pTZ18R and 2μ separated by directly repeated FRT sites, except for the insertion of a BamHI site into the FspI site at the 3' end of the FLP gene.

EXAMPLE 14

Construction of pFBY74

2 μg of pFBY29 is cleaved to completion by BamHI in CA buffer. These fragments are separated on a 0.8% LGT gel in TAE buffer. The 2.0 kbp band is cut out and the DNA is purified by ElutipD chromatography.

2 μg of pFBY24 is cleaved to completion by BamHI in CA buffer. The 5' phosphate groups are removed with 500 units of BAP in BAP buffer (50 mM Tris(hydroxymethyl) aminomethane; 50 mM NaCl; HCl to pH 8.0) at 65° C. for 30 min to prevent self ligation of the vector. These fragments are separated on a 0.8% LGT gel in TAE buffer. The 9.3 kbp band is cut out and the DNA is purified by ElutipD chromatography.

Approximately 20 ng of the prepared fragments are ligated together in the presence of 1 mM ATP and ligation buffer by 0.5 units of T4 ligase for 3 h at room temperature.

This ligation mixture is used to transform 40 μl of competent *E. coli* DH5αF' cells and plated on 2YT plates containing ampicillin, Xgal and IPTG. After 16 h incubation at 37° C., whites colonies are picked and miniscreened using BamHI and a SalI XbaI double digest to confirm the presence and orientation of the correct inserts. The LEU2 gene is in the same orientation as ampR of pFBY74.

pFBY74 is a symmetric LEU2 containing two-micron plasmid that loses the bacterial sequences in yeast.

EXAMPLE 15

Construction of plasmids pMK18 and pMK19: Two symmetric 2 micron plasmids that lose the bacterial sequences in yeast and contain the GAPFLp-hirudin expression cassette and the CUP1 gene 2 μg of plasmid pFBY4 are cleaved with EcoRI. The obtained DNA-fragment is run on a preparative 0.8% agarose gel, cut out and purified by ElutipD chromatography (Schleicher und Schüll, Dassel, Germany). The fragment is subsequently blunt-ended with 1 unit T4 polymerase in the presence of 0.05 mM each of dATP, dCTP, dGTP and dTTP for 30 min at 37° C. The polymerase is heat-inactivated at 65° C. for 10 min.

Approximately 30 ng of fragment are ligated together with 0.4 pmoles of an unphosphorylated SalI linker of the sequence GGTCGACC and 1 mM ATP by 0.5 units of T4 ligase for 3 h at room temperature. The ligation mixture is used to transform competent *E. coli* DH5αF' cells (Hanahan, D.: J. Mol. Biol. 166:557 (1983) and the cells are plated on LB medium plus ampicillin. Ampicillin resistant colonies are picked and analyzed by cutting their plasmid DNA with SalI to show the SalI linker in the previous EcoRI site. The obtained plasmid is called pMK2.

2 μg of pMK2 are cut with BamHI. The 5' phosphate groups are removed with 500 units of BAP (bovine alkaline phosphatase) in BAP-buffer at 65° C. for 30 min. The fragment is run on a preparative 0.8% agarose gel, cut out and purified by ElutipD chromatography. The fragment is subsequently blunt-ended as described above. 2 μg of pFBY5 are cleaved with SalI. The 1.1 kb fragment containing the GAPFLp-hirudin expression cassette is separated on a 0.8% agarose gel, purified and blunt-ended with T4 polymerase as described above. Approximately 22 ng of each of the prepared fragments are ligated together and the ligation mixture is transformed into competent DH5αF' cells as described above. Ampicillin resistant colonies are picked and analyzed using PstI to confirm the presence of the correct insert and to determine the orientation. The generated plasmids are called pMK12 and pMK13. pMK12 contains the GAPFLp-hirudin expression cassette in the reverse orientation as compared to the URA3 gene, whereas pMK13 contains the respective genes in the same orientation.

2 μg of pFBY74 are cut with SnaBI. The 5' phosphate groups are removed with BAP and the obtained DNA-fragment is purified via an 0.8% agarose gel and ElutipD chromatography as described above. 2 μg of pMK12 are cut with SalI. The 2.3 kb fragment, containing the GAPFLp-hirudin expression cassette and the URA3 gene is gel-purified and blunt-ended as described above. Approximately 20 ng of each, cut pFBY74 and the pMK12 fragment are ligated together and transformed into competent DH5αF' cells as described above. Ampicillin resistant colonies are analyzed cutting their plasmid DNA with SalI and NcoI to confirm the correct insert and to determine the orientation. Two plasmids are obtained called pMK14 and pMK15. The difference between these two plasmids is that in the former the GAPFLp-hirudin expression cassette has the reverse and the latter the same orientation as compared to the LEU2 gene.

Figure 4:
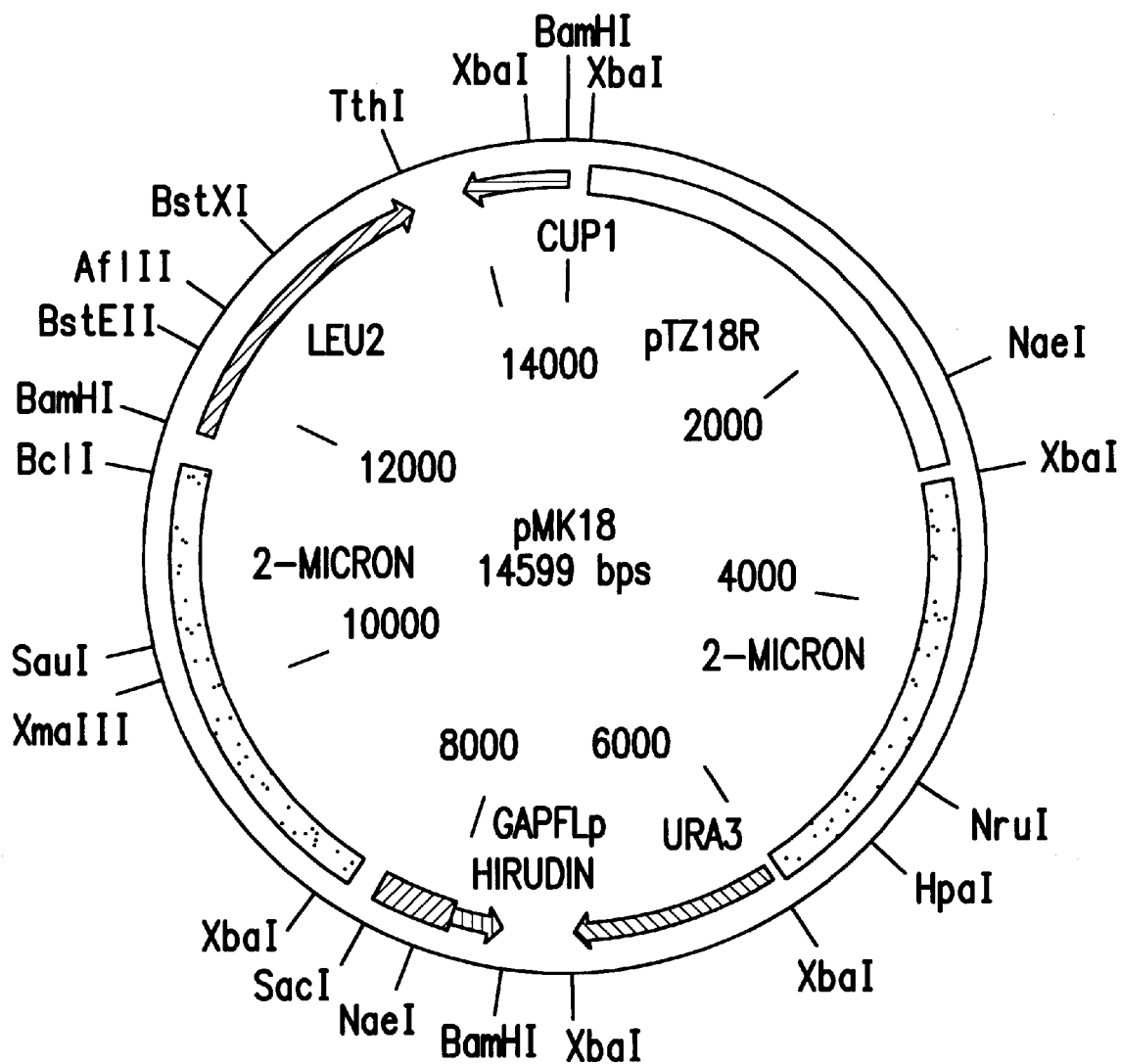
FIG. 4 is a schematic illustration of plasmid pMK18.
Figure 5:
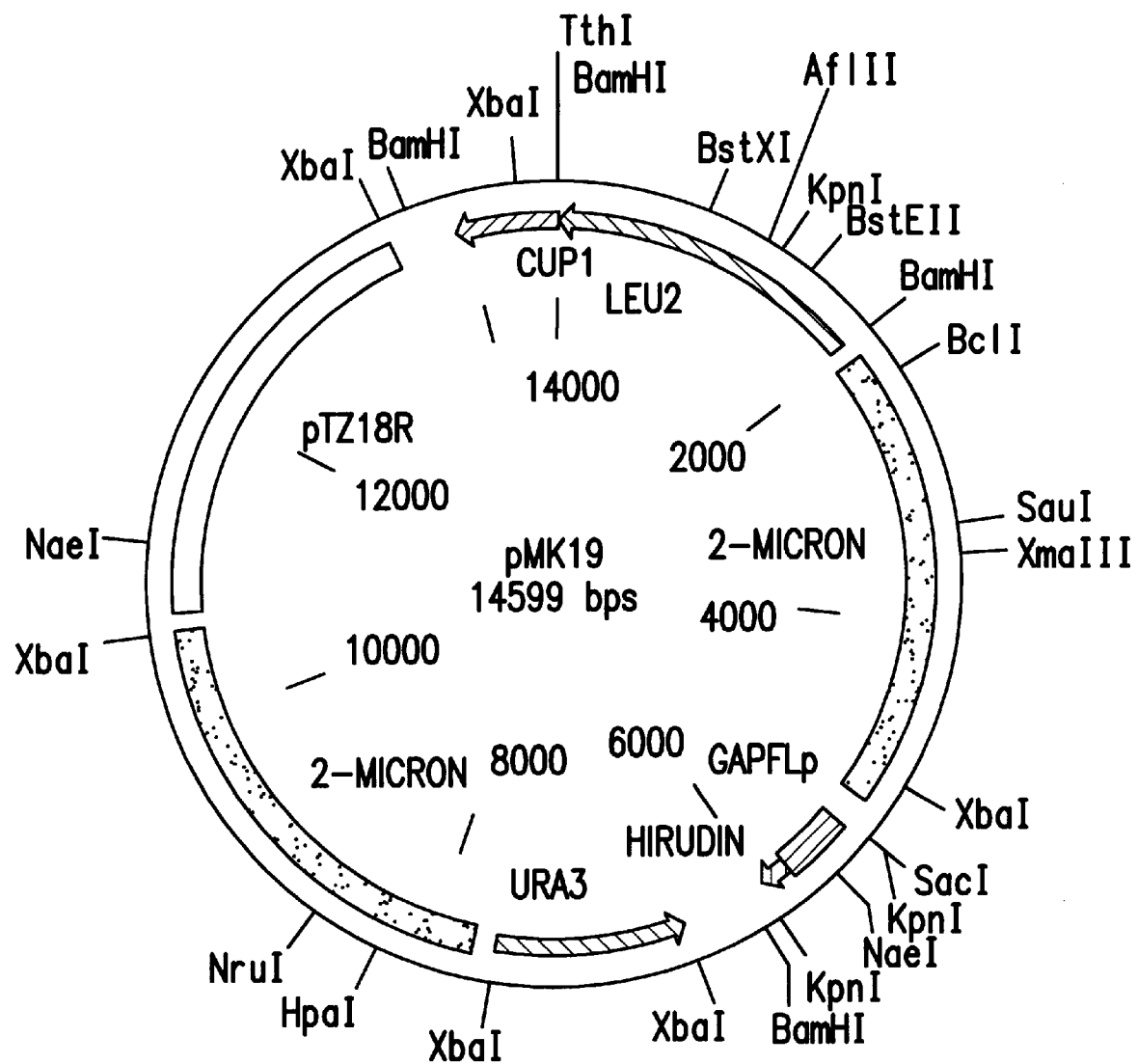
FIG. 5 is a schematic illustration of plasmid pMK19.

2 μg pMK14 are cut with SalI. The 5' phosphate groups are removed with BAP and the DNA-fragment is gel-purified as described above. The fragment is subsequently blunt-ended with T4 polymerase. 2 μg of pHE105 (see example 1) is cut with KpnI. The 940 bp fragment containing the CUP1 gene including its own promoter is separated on a 1% agarose gel, purified and blunt-ended with T4 polymerase as described above. Approximately 20 ng of each of the prepared fragments are ligated together by T4 ligase as described. The ligation mixture is used to transform DH5αF' cells. Ampicillin resistant colonies are picked and their plasmid DNA analyzed using BamHI to confirm the presence of the correct insert and the orientation. The obtained plasmids are called pMK18 and pMK19 (FIGS. 4 and 5). The difference between these two plasmids is that in the former the CUP1 gene has the same and in the latter the reverse orientation as compared to the GAPFLp-hirudin expression cassette.

EXAMPLE 16

Construction of plasmids pMK26 and pMK27: Two symmetric 2micron plasmids that loose the bacterial sequences in yeast and contain the CUP1p-hirudin expression cassette and the CUP1 gene 2 µg of pMK2 (see example 15) are cut with BamHI. The 5' phosphate groups are removed with 500 units of BAP (bovine alkaline phosphatase) in BAP-buffer at 65° C. for 30 min. The fragment is run on a preparative 0.8% agarose gel, cut out and purified by ElutipD chromatography (Schleicher und Schüll, Dassel, Germany). The fragment is subsequently blunt-ended with 1 unit T4 polymerase in the presence of 0.05 mM each of dATP, dCTP, dGTP and dTTP for 30 min at 37° C. The polymerase is heat-inactivated at 65° C. for 10 min.

2 µg of pPFY53 (see example 2) are cleaved with SalI. The 1.3 kb fragment containing the CUP1p-hirudin expression cassette is separated on a 0.8% agarose gel, purified and blunt-ended with T4 polymerase as described above. Approximately 20 ng of each of the prepared fragments are ligated together in the presence of 1 mM ATP by 0.5 units of T4 ligase for 3 h at room temperature. The ligation mixture is used to transform competent E. coli DH5αF' cells (Hanahan, D.: J. Mol. Biol. 166:557 (1983)) and the cells are plated on LB medium plus ampicillin. Ampicillin resistant colonies are picked and analyzed using XbaI to confirm the presence of the correct insert and to determine the orientation. The generated plasmids are called pMK3/1 and pMK3/2. pMK3/1 contains the CUP1p-hirudin expression cassette in the same orientation as compared to the URA3 gene, whereas pMK3/2 contains the respective genes in the reverse orientation.

2 µg of pFBY74 are cut with SnaBI. The 5' phosphate groups are removed with BAP and the obtained DNA-fragment is purified via an 0.8% agarose gel and ElutipD chromatography as described above. 2 µg of pMK3/2 are cut with SalI. The 2.6 kb fragment, containing the CUP1p-hirudin expression cassette and the URA3 gene is gel-purified and blunt-ended as described above. Approximately 20 ng of each, cut pFBY74 and the pMK3/2 fragment are ligated together and transformed into competent E. coli DH5αF' cells as described above. Ampicillin resistant colonies are analyzed cutting their plasmid DNA with SalI and NcoI to confirm the correct insert and to determine the orientation. Two plasmids are obtained called pMK5x1 and pMK5x2. The difference between these two plasmids is that in the former the CUP1p-hirudin expression cassette has the reverse and the latter the same orientation as compared to the LEU2 gene.

Figure 6:
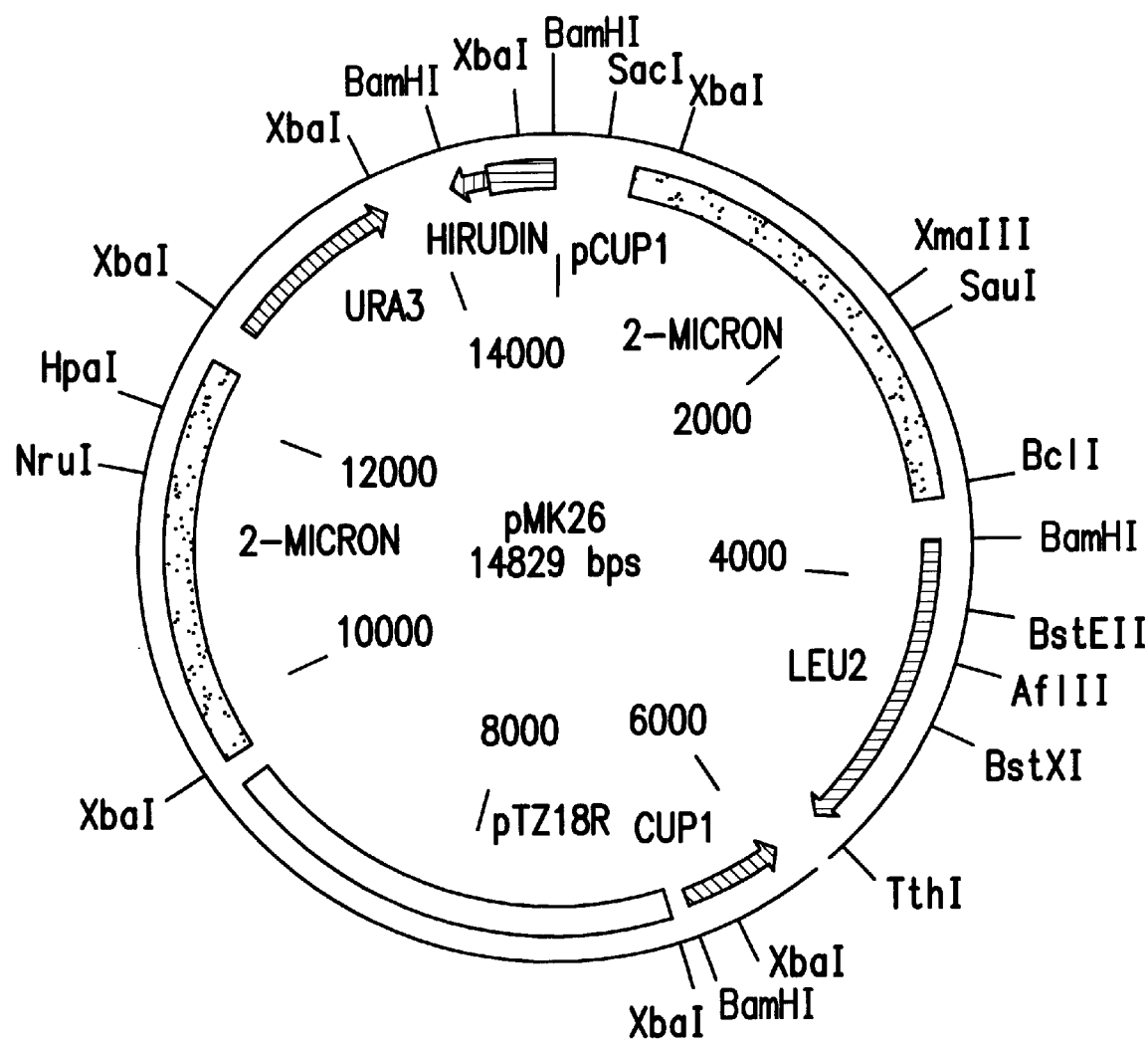
FIG. 6 is a schematic illustration of plasmid pMK26.
Figure 7:
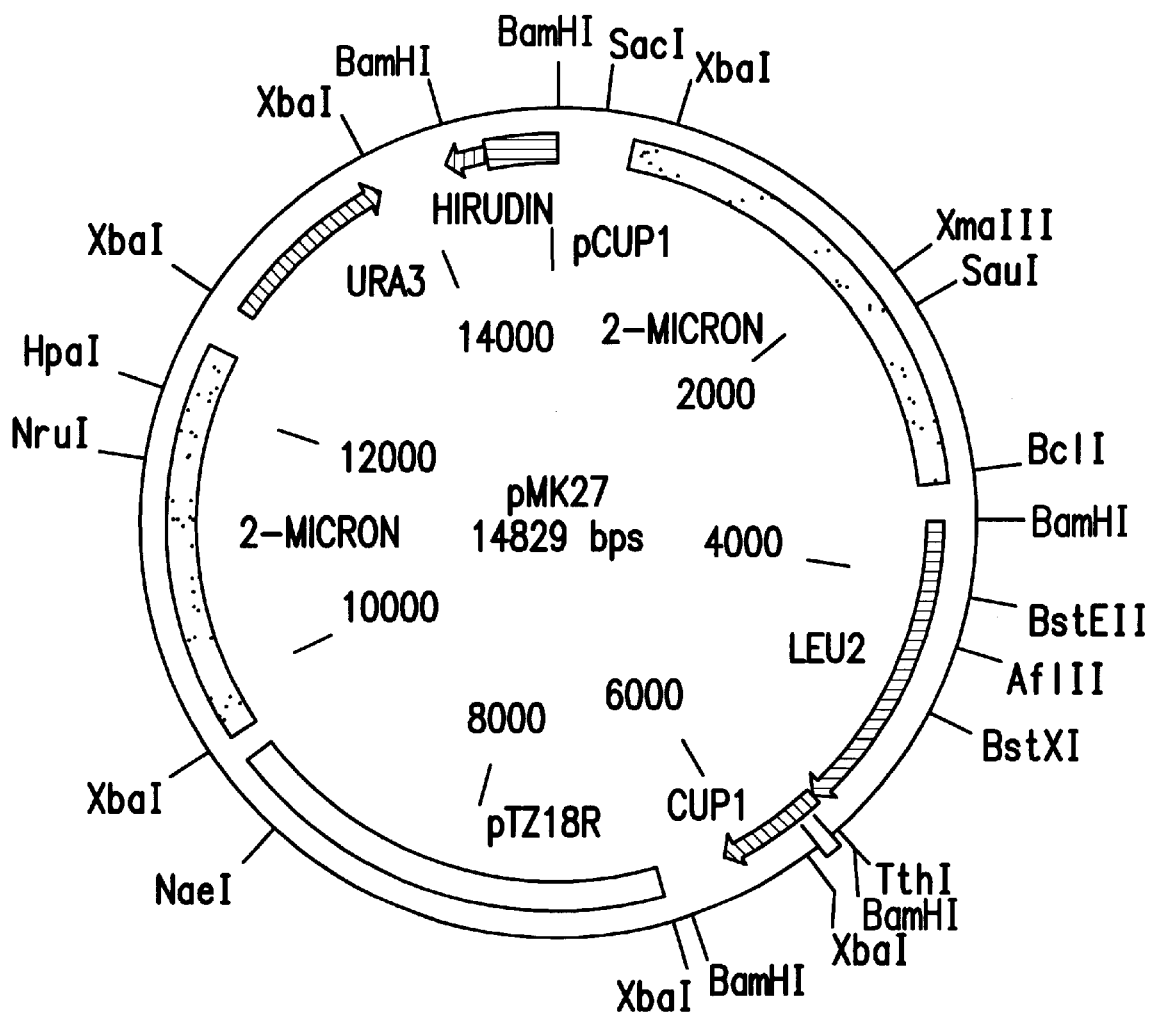
FIG. 7 is a schematic illustration of plasmid pMK27.

2 µg pMK5x1 are cut with SalI. The 5' phosphate groups are removed with BAP and the DNA-fragment is gel-purified as described above. The fragment is subsequently blunt-ended with T4 polymerase. 2 µg of pHE105 (see example 1) are cut with KpnI. The 940 bp fragment containing the CUP1 gene including its own promoter is separated on a 1% agarose gel, purified and blunt-ended with T4 polymerase as described above. Approximately 20 ng of each of the prepared fragments are ligated together by T4 ligase as described. The ligation mixture is used to transform E. coli DH5αF' cells. Ampicillin resistant colonies are picked and their plasmid DNA analyzed using BamHI to confirm the presence of the correct insert and the orientation. The obtained plasmids are called pMK26 and pMK27 (FIGS. 6 and 7). The difference between these two plasmids is that in the former the CUP1 gene has the same and in the latter the reverse orientation as compared to the CUP1p-hirudin expression cassette.

Deposition of microorganisms

The following microorganism strains were deposited at the Deutsche Sammlung von Mikroorganismen (DSM), Mascheroder Weg 1b, D-3300 Braunschweig (accession numbers and deposition dates given):

| | |
|---|---|
| Saccharomyces cerevisiae H449 | DSM 4413 February 18, 1988 |
| Saccharomyces cerevisiae HT462/TH3 | DSM 7190 July 22, 1992 |
| E. coli DH5αF'/pDP34 | DSM 4473 March, 14 1988 |
| E. coli DH5αF'/pFBY2 | DSM 6271 December 14, 1990 |
| E. coli DH5αF'/pFBY4 | DSM 6272 December 14, 1990 |
| E. coli DH5αF'/pFBY5 | DSM 6273 December 14, 1990 |
| E. coli DH5αF'/pFBY29 | DSM 6275 December 14, 1990 |

We claim:

1. A method for the production of a biologically active polypeptide comprising culturing in a complex culture medium a yeast strain which contains not more than one functional CUP1 gene in the genome and harbors a yeast two micron-derived plasmid comprising a functional CUP1 gene and a polypeptide expression cassette, and isolating the produced polypeptide; wherein the culture medium is supplied with a CUP1 promoter inducing amount of a copper salt; and further wherein the polypeptide expression cassette consists of a yeast promoter operably linked to a first DNA sequence encoding a yeast signal peptide linked in the proper reading frame to a second DNA sequence coding for the polypeptide, and a DNA sequence containing yeast transcription termination signals wherein said polypeptide is desulphatohirudin.

2. A method according to claim 1 wherein the promoter is the yeast CUP1 promoter.

3. A method according to claim 1 wherein the promoter is the yeast GAPFL promoter.

4. A method according to claim 1 wherein the polypeptide is desulphatohirudin variant HV1.

5. A method according to claim 1 wherein the yeast strain is a strain of *Saccharomyces cerevisiae*.

6. A method according to claim 1 wherein the yeast strain is single or multiple protease-deficient.

7. A method according to claim 1 wherein the yeast strain lacks genomic CUP1 gene product activity.

8. A yeast two micron-derived hybrid plasmid comprising the functional CUP1 gene and a polypeptide expression cassette, wherein the polypeptide expression cassette consists of a yeast promoter operably linked to a first DNA sequence encoding a yeast signal peptide linked in the proper reading frame to a second DNA sequence coding for the polypeptide, and a DNA sequence containing yeast transcription termination signals, and wherein the polypeptide is desulphatohirudin.

9. A yeast plasmid according to claim 8, wherein the promoter is selected from the group consisting of the GAPFL and the yeast CUP1 promoter.

10. A yeast plasmid according to claim 8, wherein the promoter is the yeast CUP1 promoter.

11. A yeast plasmid according to claim 8 wherein the DNA sequence encoding a signal peptide is selected from the group consisting of the signal and prepro sequences of the yeast invertase, α-factor, pheromone peptidase (KEX1), "killer toxin" and repressible acid phosphatase (PHO5) genes and the glucoamylase signal sequence from *Aspergillus awamori*.

12. A yeast plasmid according to claim 8 wherein the DNA sequence encoding a signal peptide is selected from the group consisting of the signal sequence of the yeast invertase and PHO5 gene.

13. A yeast plasmid according to claim 8 wherein the DNA sequence containing yeast transcription termination signals is the 3' flanking sequence of a yeast gene which contains proper signals for transcription termination and polyadenylation.

14. A yeast plasmid according to claim 8 comprising the 1311 bp BamHI fragment, comprising the CUP1 promoter, the CUP1 coding region and the CUP1 terminator, as shown in SEQ ID NO:1.

15. A yeast plasmid according to claim 8 comprising the complete two-micron DNA.

16. A yeast plasmid according to claim 8 exhibiting symmetry and lacking bacterial sequences.

17. A yeast plasmid according to claim 8 comprising 1 to 3 additional polypeptide expression cassettes.

18. A yeast strain comprising not more than one functional CUP1 gene in the genome and harboring a yeast hybrid plasmid according to claim 8 comprising a polypeptide expression cassette and the functional CUP1 gene; which yeast strain additionally lacks genomic CUP1 gene product activity.

19. A yeast plasmid comprising a 1082 bp BamHI/SalI fragment comprising a CUP1 promoter, a PHO5 leader sequence, a hirudin gene and a PHO5 terminator, as shown in SEQ ID NO:3.

20. A yeast two micron-derived hybrid plasmid comprising a functional CUP1 gene and a polypeptide expression cassette and a transcriptional activator ACE1 expression cassette.

* * * * *